US007491489B2

(12) United States Patent
Zheng et al.

(10) Patent No.: US 7,491,489 B2
(45) Date of Patent: Feb. 17, 2009

(54) SYNTHETIC PEPTIDE TARGETING CRITICAL SITES ON THE SARS-ASSOCIATED CORONAVIRUS SPIKE PROTEIN RESPONSIBLE FOR VIRAL INFECTION AND METHOD OF USE THEREOF

(75) Inventors: Bojian Zheng, Hong Kong (CN); Yi Guan, Hong Kong (CN); Jiandong Huang, Hong Kong (CN); Ming-Liang He, Hong Kong (CN)

(73) Assignee: The University of Hong Knog, Hong Kong (CN)

( * ) Notice: Subject to any disclaimer, the term of this patent is extended or adjusted under 35 U.S.C. 154(b) by 299 days.

(21) Appl. No.: 11/262,044

(22) Filed: Oct. 28, 2005

(65) Prior Publication Data

US 2006/0110758 A1    May 25, 2006

Related U.S. Application Data

(60) Provisional application No. 60/630,334, filed on Nov. 22, 2004.

(51) Int. Cl.
  C12Q 1/00    (2006.01)
  C12Q 1/18    (2006.01)
  C12Q 1/70    (2006.01)
  G01N 33/53   (2006.01)
(52) U.S. Cl. .............................. 435/4; 435/5; 435/7.1; 435/7.21
(58) Field of Classification Search ....................... None
  See application file for complete search history.

(56) References Cited

U.S. PATENT DOCUMENTS 7,053,179 B2 *  5/2006  Root et al. ................... 530/350
2004/0229219 A1 * 11/2004  Gallaher et al. ............... 435/5

FOREIGN PATENT DOCUMENTS

WO    WO 2005016238    *  2/2005

OTHER PUBLICATIONS

Bosch et al. "Severe acute respiratory syndrome coronavirus (SARS-CoV) infection inhibition using spike protein heptad repeat-derived peptides," Proceedings of the National Academy of Sciences, USA, vol. 101 No. 22, pp. 8455-8460 (Jun. 2004).*
Ho et al., "Design and biological activities of novel inhibitory peptides for SARS-CoV spike protein and angiotensin-converting enzyme-2 interaction," Antiviral Research, vol. 69, pp. 70-76 (2006).*
Xiao et al., "The SARS-CoV S glycoprotein: expression and functional characterization," Biochemical and Biophysical Research Communications, vol. 312 pp. 1159-1164 (2003).*
Yuan et al., "Suppression of SARS-CoV entry by peptides corresponding to heptad regions on spike glycoprotein," Biochemical and Biophysical Resaerch Communications, vol. 319, pp. 746-752 (2004).*
Zhao et al., "A study on antigenicity and receptor-binding ability of fragment 450-650 of the spike protein of SARS coronavirus," Virology, vol. 359 No. 2, pp. 362-370 (Mar. 2007).*
GenPept Accession AAP41037 "spike glycoprotein [SARS coronavirus Tor2]" Mar. 2004.*
Babcock, Gregory J. et al., "Amino Acids 270 to 510 of the Severe Acute Respiratory Syndrome Coronavirus Spike Protein Are Required for Interaction with Receptor", *J. Virol.* 78, 4552-4560 (2004).
Berendsen, H.J.C. et al., GROMACS: "A message-passing parallel molecular dynamics implementation", *Comp. Phys. Comm.* 91, 43-56 (1995).
Berman, Helen M. et al., "The Protein Data Bank", *Nucleic Acids Research* 28, 235-242 (2000).
Bernini, Andrea et al., "Prediction of quaternary assembly of SARS coronavirus peplomer", *Biochem. Biophys. Res. Communi.* 325, 1210-1214 (2004).
Delmas, Bernard and Laude, Hubert, "Assembly of Coronavirus Spike Protein into Trimers and Its Role in Epitope Expression", *J. Virol.* 64, 5367-5375 (1990).
Derdeyn, Cynthia A. et al., "Sensitivity of Human Immunodeficiency Virus Type 1 to Fusion Inhibitors Targeted to the gp41 First Heptad Repeat Involves Distinct Regions of gp41 and Is Consistently Modulated by gp120 Interactions with the Coreceptor", *J. Virol.* 75, 8605-8614 (2001).
Fouchier, R.A. et al., "Koch's postulates fulfilled for SARS virus", *Nature* 423, 240 (2003).
Gallagher, Thomas M., "A Role for Naturally Occurring Variation of the Murine Coronavirus Spike Protein in Stabilizing Association with the Cellular Receptor", *J. Virol.* 71, 3129-3137 (1997).
Guan, Y. et al., "Molecular epidemiology of the novel coronavirus that causes severe acute respiratory syndrome", *Lancet* 363, 99-104 (2004).
Guan, Y. et al., "Isolation and Characterization of Viruses Related to the SARS Coronavirus from Animals in Southern China", *Science* 302, 276-278 (2003).
He, Ming-Liang et al., "Induction of apoptosis and inhibition of cell growth by developmental regulator hTBX5", *Biochem. Biophys. Res. Commun.* 297, 185-192 (2002).
He, Ming-Liang et al., "A new and sensitive method for the quantification of HBV cccDNA by real-time PCR", *Biochem. Biophys. Res. Commun.* 295, 1102-1107 (2002).

(Continued)

*Primary Examiner*—Zachariah Lucas
(74) *Attorney, Agent, or Firm*—Saliwanchik, Lloyd & Saliwanchik

(57) ABSTRACT

The present invention provides methods for locating critical portions or sites on the spike protein (S protein) of SARS-associated coronavirus (SARS-CoV) responsible for the viral infection that causes Severe Acute Respiratory Syndrome (SARS). The present invention also provides new synthetic peptides targeting such critical portions or sites of the S protein of SARS-CoV for preventing or treating of SARS-CoV infection in a subject. The present invention further provides methods of testing antiviral activity exerted by antiviral agents using real-time quantitative PCR.

2 Claims, 12 Drawing Sheets
(2 of 12 Drawing Sheet(s) Filed in Color)

OTHER PUBLICATIONS

Ho, Tin-Yun et al., "Antigenicity and receptor-binding ability of recombinant SARS coronavirus spike protein", *Biochem. Biophys. Res. Commun.* 313, 938-947 (2004).

Holland, John J. et al., "Quantitation of Relative Fitness and Great Adaptability of Clonal Populations of RNA Viruses", *J. Virol.* 65, 2960-2967 (1991).

Holmes, Kathryn V. et al., "Receptor Specificity and Receptor-Induced Conformational Changes in Mouse Hepatitis Virus Spike Glycoprotein", *Adv. Exp. Med. Biol.* 494, 173-181 (2001).

Koradi, Reto et al., "MOLMOL: A program for display and analysis of macromolecular structures", *J. Mol. Graph.* 14, 51-55 (1996).

Lewicki, Daniel N. and Gallagher, Thomas M., "Quaternary Structure of Coronavirus Spikes in Complex with Carcinoembryonic Antigen-related Cell Adhesion Molecule Cellular Receptors", *J. Biol. Chem.* 277, 19727-19734 (2002).

Li, Wenhui et al., "Angiotensin-converting enzyme 2 is a functional receptor for the SARS coronavirus", *Nature* 426, 450-454 (2003).

Lin, Yun et al., "Probing the structure of the SARS coronavirus using scanning electron microscopy", *Antiviral Therapy* 9, 287-289 (2004).

Liu, Shuwen et al., "Interaction between heptad repeat 1 and 2 regions in spike protein of SARS-associated coronavirus: implications for virus fusogenic mechanism and identification of fusion inhibitors", *Lancet.* 363, 938-947 (2004).

Matsuyama, Shutoku and Taguchi, Fumihiro, "Communication between S1N330 and a Region in S2 of Murine Coronavirus Spike Protein is Important for Virus Entry into Cells Expressing CEACAM 1b Receptor", *Virology* 295, 160-171 (2002).

Medinas R.J. et al., "C-Terminal gp40 Peptide Analogs Inhibit Feline Immunodeficiency Virus: Cell Fusion and Virus Spread", *J. Virol.* 76, 9079-9086 (2002).

Peiris, JSM. et al., "Inhibition of SARS-Associated Coronavirus Infection and Replication by RNA Interference", *JAMA* 290, 2665-2666 (2003).

Peiris, JSM. et al., "Coronavirus as a possible cause of severe acute respiratory syndrome", *Lancet* 361, 1319-1325 (2003).

Piñón, Josephina D. et al., "An Antiviral Peptide Targets a Coiled-Coil Domain of the Human T-Cell Leukemia Virus Envelope Glycoprotein", *J. Virol.* 77, 3281-3290 (2003).

Rota, Paul A. et al., "Characterization of a Novel Coronavirus Associated with Severe Acute Respiratory Syndrome", *Science* 300, 1394-1399 (2003).

Sauter, Nicholas K. et al., "Binding of Influenza Virus Hemagglutinin to Analogs of Its Cell-Surface Receptor, Sialic Acid: Analysis of Proton Nuclear Magnetic Resonance Spectroscopy and X-ray Crystallography", *Biochemistry* 31, 9609-9621 (1992).

Sia, Samuel K. et al., "Short constrained peptides that inhibit HIV-1 entry", *Proc. Natl. Acad. Sci. USA* 99, 14664-14669 (2002).

Sippl, Manfred J., "Recognition of Errors in Three-Dimensional Structures of Proteins", *Proteins* 17, 355-362 (1993).

Spiga, Ottavia et al., "Molecular modelling of S1 and S2 subunits of SARS coronavirus spike glycoprotein", *Biochem. Biophys. Res. Commun.* 310, 78-83 (2003).

Stein, Lincoln D. et al., "The Genome Sequence of *Caenorhabditis briggsae*: A Platform for Comparative Genomics", *PLoS Biology* 1, 166-192 (2003).

Sturman, Lawrence S. et al., "Conformational Change of the Coronavirus Peplomer Glycoprotein at pH 8.0 and 37° C. Correlates with Virus Aggregation and Virus-Induced Cell Fusion", *J. Virol.* 64, 3042-3050 (1990).

Sui, Jianhua et al., "Potent neutralization of severe acute respiratory syndrome (SARS) coronavirus by a human mAb to S1 protein that blocks receptor association", *Proc. Natl. Acad. Sci. USA* 101, 2536-2541 (2004).

Taguchi, Fumihiro and Shimazaki, Yohko K., "Functional analysis of an epitope in the S2 subunit of the murine coronavirus spike protein: involvement in fusion activity", *J. Gen. Virol.* 81, 2867-2871 (2000).

Tripet, Brian et al., "Structural Characterization of the SARS-Coronavirus Spike S Fusion Protein Core", *J. Biol. Chem.* 279, 20836-20849 (2004).

Wong, Swee Kee et al., "A 193-Amino Acid Fragment of the SARS Coronavirus S Protein Efficiently Binds Angiotensin-converting Enzyme 2", *J. Biol. Chem.* 279, 3197-3201 (2004).

Zheng, Bo Jian et al., "SARS-related Virus Predating SARS Outbreak, Hong Kong", *Emerg. Infect. Dis.* 10, 176-178 (2004).

Zhong, N.S. et al., "Epidemiology and cause of severe acute respiratory syndrome (SARS) in Guangdong, People's Republic of China, in Feb. 2003", *Lancet* 362, 1353-1358 (2003).

World Health Organization ("WHO"), *Communicable Disease Surveillance & Response (CSR): Severe Acute Respiratory Syndrome.* www.who.int/csr/sars/en, 2004.

The Chinese SARS Molecular Epidemiology Consortium, "Molecular Evolution Of The SARS Coronavirus During The Course of the SARS Epidemic in China", *Sciencexpress*, www.sciencexpress.org, p. 1 (Jan. 29, 2004).

\* cited by examiner

Figure 1

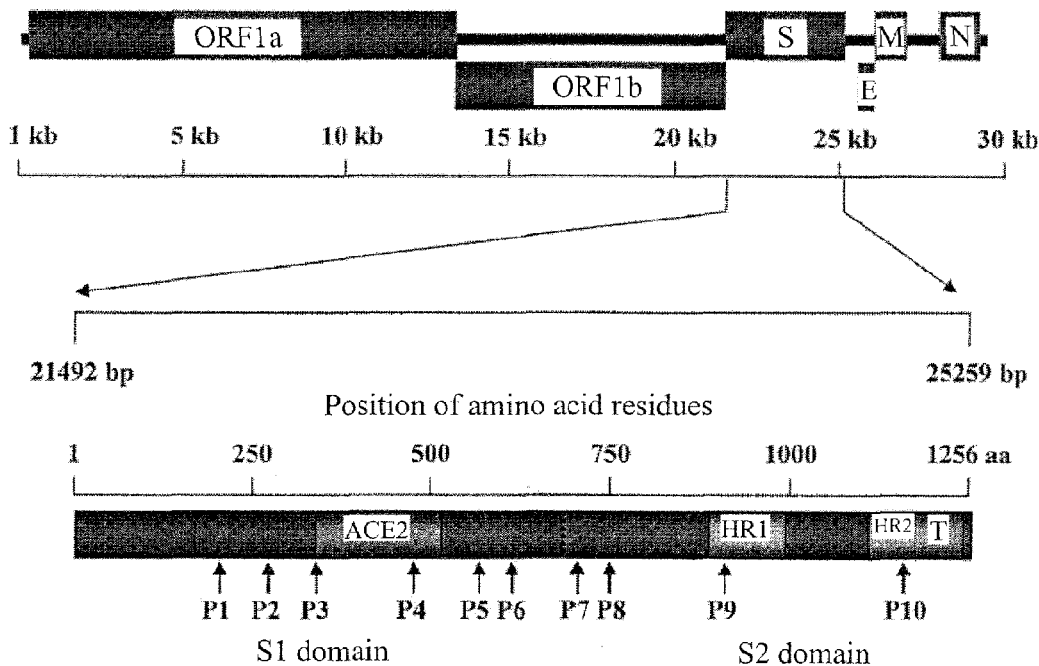

| No. | Sequence | Position |
|---|---|---|
| P1 | FKLPLGIN(K)ITNFRAILTAFS(L) (SEQ ID NO:16) | 220-239 |
| P2 | **PT*T*(K)FMLKYDENGTITDAVDC (SEQ ID NO:17) | 259-278** |
| P3 | VLYNST*F*(S)FSTFKCYGVSATK (SEQ ID NO:18) | 354-373 |
| P4 | PALNCYWPL*N*(K)DYGFYTTSGI (SEQ ID NO:19) | 470-489 |
| P5 | RDVSD*F*(I)TDSVRDPKTSEILD (SEQ ID NO:20) | 553-572 |
| P6 | **YQDVNCTDV*S*(P)TAIHADQLTP (SEQ ID NO:21) | 598-617** |
| P7 | SNNTIAIPTNF*S*(L)ISITTEVM (SEQ ID NO:22) | 690-709 |
| P8 | **QYGSFC*T*(A)QLNRALSGIA*A*(V)EQ (SEQ ID NO:23) | 737-756** |
| P9 | GIGV*T*(A)QNVLYENQKQIANQF (SEQ ID NO:24) | 890-909 |
| P10 | **IQ*K*(E)EIDRLNEVAKNLNESLI (SEQ ID NO:25) | 1161-1180** |

Figures 2A-2F
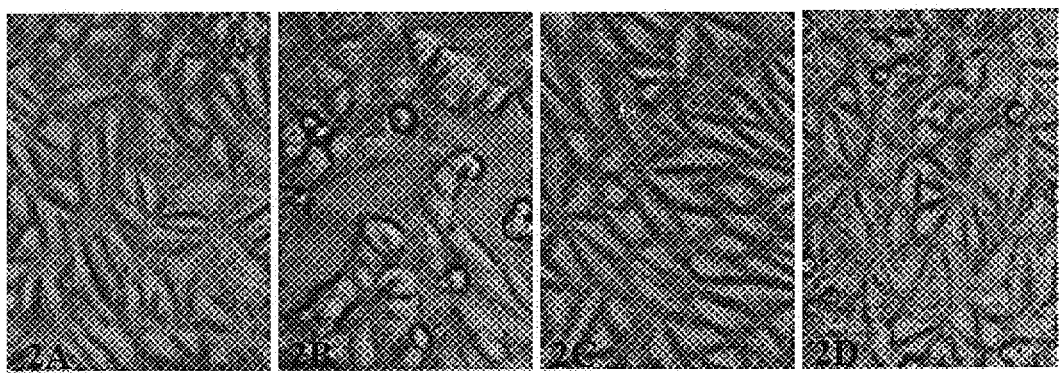
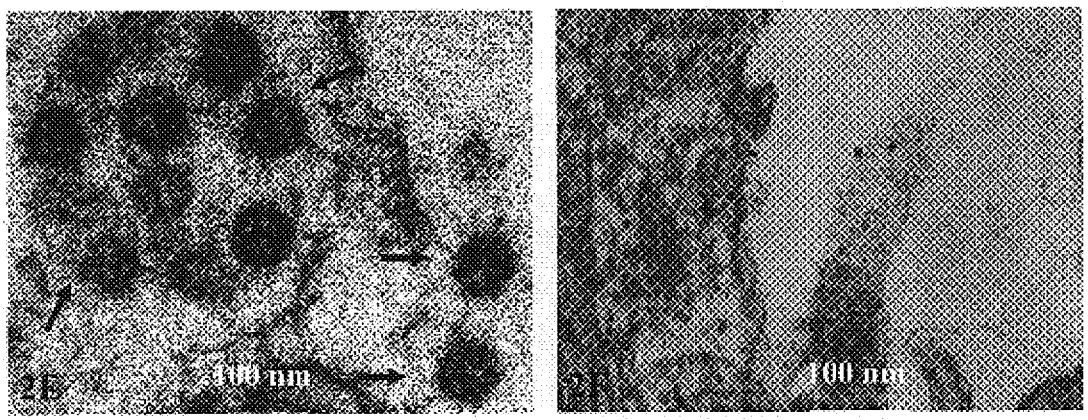

Figure 8A
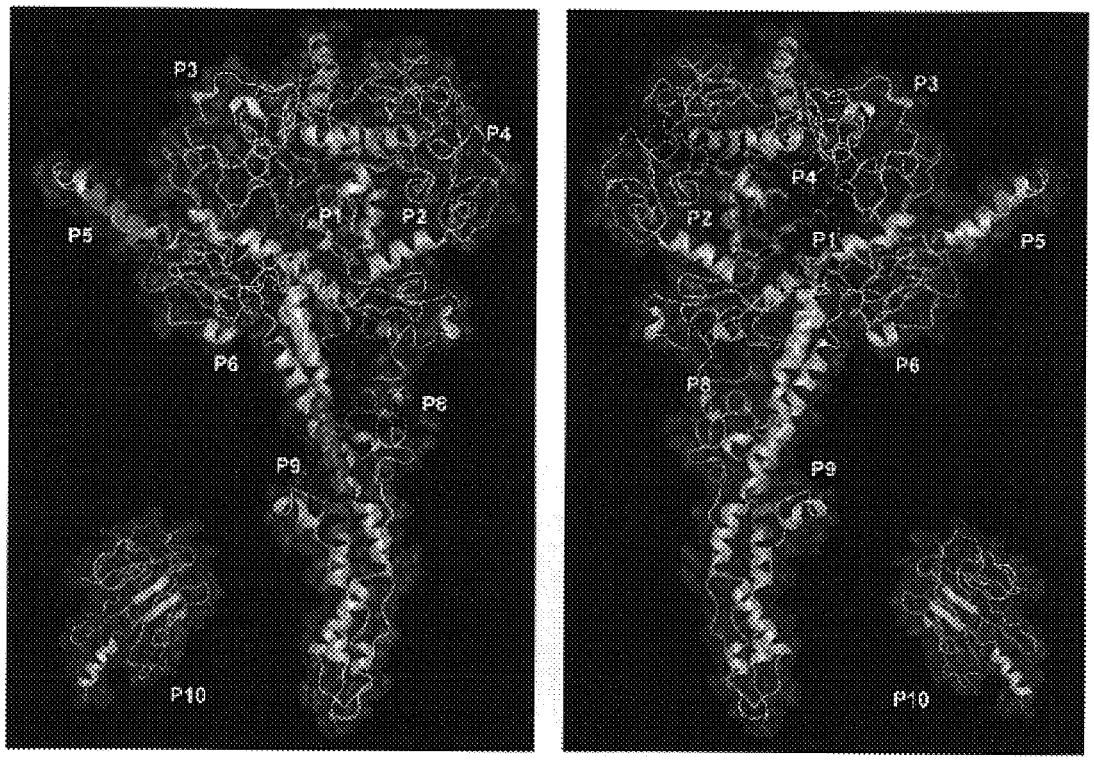
| Figure 8B | Figure 8C | Figure 8D | Figure 8E |
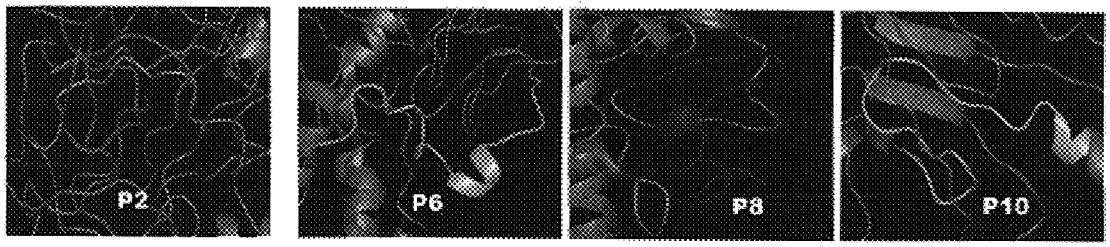

Fusion

Fusion

Fusion

SEQUENCE LISTING

<160> NUMBER OF SEQ ID NOS: 25

<210> SEQ ID NO 1
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Phe Lys Leu Pro Leu Gly Ile Asn Ile Thr Asn Phe Arg Ala Ile
 1               5                  10                  15

Leu Thr Ala Phe Ser
            20

<210> SEQ ID NO 2
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Pro Thr Thr Phe Met Leu Lys Tyr Asp Glu Asn Gly Thr Ile Thr
 1               5                  10                  15

Asp Ala Val Asp Cys
            20

<210> SEQ ID NO 3
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Val Leu Tyr Asn Ser Thr Phe Phe Ser Thr Phe Lys Cys Tyr Gly
 1               5                  10                  15

Val Ser Ala Thr Lys
            20

<210> SEQ ID NO 4
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Pro Ala Leu Asn Cys Tyr Trp Pro Leu Asn Asp Tyr Gly Phe Tyr
 1               5                  10                  15

Thr Thr Ser Gly Ile
            20

<210> SEQ ID NO 5
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 5

Arg Asp Val Ser Asp Phe Thr Asp Ser Val Arg Asp Pro Lys Thr
1               5                   10                  15

Ser Glu Ile Leu Asp
            20

<210> SEQ ID NO 6
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Tyr Gln Asp Val Asn Cys Thr Asp Val Ser Thr Ala Ile His Ala
1               5                   10                  15

Asp Gln Leu Thr Pro
            20

<210> SEQ ID NO 7
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ser Asn Asn Thr Ile Ala Ile Pro Thr Asn Phe Ser Ile Ser Ile
1               5                   10                  15

Thr Thr Glu Val Met
            20

<210> SEQ ID NO 8
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gln Tyr Gly Ser Phe Cys Thr Gln Leu Asn Arg Ala Leu Ser Gly
1               5                   10                  15

Ile Ala Ala Glu Gln
            20

<210> SEQ ID NO 9
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Ile Gly Val Thr Gln Asn Val Leu Tyr Glu Asn Gln Lys Gln
1               5                   10                  15

Ile Ala Asn Gln Phe
            20

```
<210> SEQ ID NO 10
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ile Gln Lys Glu Ile Asp Arg Leu Asn Glu Val Ala Lys Asn Leu
 1               5                  10                  15

Asn Glu Ser Leu Ile
                20

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gcttaggccc tttgagagag aca                                             23

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gccaatgcca gtagtggtgt aaa                                             23

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cctgatggca aaccttgcac                                                 20

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ctaatgtgcc tttctcccct gatggca                                         27

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
```
cacctgctct taattgttat tggcc                                    25

<210> SEQ ID NO 16
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Asn or Lys
<220> FEATURE:
<221> NAME/KEY: MOD_RES
<222> LOCATION: (20)
<223> OTHER INFORMATION: Ser or Leu

<400> SEQUENCE: 16

Phe Lys Leu Pro Leu Gly Ile Xaa Ile Thr Asn Phe Arg Ala Ile Leu
 1               5                  10                  15

Thr Ala Phe Xaa
            20

<210> SEQ ID NO 17
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Thr or Lys

<400> SEQUENCE: 17

Pro Thr Xaa Phe Met Leu Lys Tyr Asp Glu Asn Gly Thr Ile Thr Asp
 1               5                  10                  15

Ala Val Asp Cys
            20

<210> SEQ ID NO 18
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)
<223> OTHER INFORMATION: Phe or Ser

<400> SEQUENCE: 18

Val Leu Tyr Asn Ser Thr Xaa Phe Ser Thr Phe Lys Cys Tyr Gly Val
 1               5                  10                  15

Ser Ala Thr Lys
            20

<210> SEQ ID NO 19
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES

```
<222> LOCATION: (10)
<223> OTHER INFORMATION: Asn or Lys

<400> SEQUENCE: 19

Pro Ala Leu Asn Cys Tyr Trp Pro Leu Xaa Asp Tyr Gly Phe Tyr Thr
 1               5                  10                  15

Thr Ser Gly Ile
            20

<210> SEQ ID NO 20
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)
<223> OTHER INFORMATION: Phe or Ile

<400> SEQUENCE: 20

Arg Asp Val Ser Asp Xaa Thr Asp Ser Val Arg Asp Pro Lys Thr Ser
 1               5                  10                  15

Glu Ile Leu Asp
            20

<210> SEQ ID NO 21
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)
<223> OTHER INFORMATION: Ser or Pro

<400> SEQUENCE: 21

Tyr Gln Asp Val Asn Cys Thr Asp Val Xaa Thr Ala Ile His Ala Asp
 1               5                  10                  15

Gln Leu Thr Pro
            20

<210> SEQ ID NO 22
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)
<223> OTHER INFORMATION: Ser or Leu

<400> SEQUENCE: 22

Ser Asn Asn Thr Ile Ala Ile Pro Thr Asn Phe Xaa Ile Ser Ile Thr
 1               5                  10                  15

Thr Glu Val Met
            20

<210> SEQ ID NO 23
<211> LENGTH: 20
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (7)
<223> OTHER INFORMATION: Thr or Ala
<220> FEATURE:
<221> NAME/KEY: MOD_RES
<222> LOCATION: (18)
<223> OTHER INFORMATION: Ala or Val

<400> SEQUENCE: 23

Gln Tyr Gly Ser Phe Cys Xaa Gln Leu Asn Arg Ala Leu Ser Gly Ile
 1               5                  10                  15

Ala Xaa Glu Gln
            20

<210> SEQ ID NO 24
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: Thr or Ala

<400> SEQUENCE: 24

Gly Ile Gly Val Xaa Gln Asn Val Leu Tyr Glu Asn Gln Lys Gln Ile
 1               5                  10                  15

Ala Asn Gln Phe
            20

<210> SEQ ID NO 25
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Lys or Glu

<400> SEQUENCE: 25

Ile Gln Xaa Glu Ile Asp Arg Leu Asn Glu Val Ala Lys Asn Leu Asn
 1               5                  10                  15

Glu Ser Leu Ile
            20
```

SYNTHETIC PEPTIDE TARGETING CRITICAL SITES ON THE SARS-ASSOCIATED CORONAVIRUS SPIKE PROTEIN RESPONSIBLE FOR VIRAL INFECTION AND METHOD OF USE THEREOF

This application claims the benefit of provisional application U.S. Ser. No. 60/630,334, filed Nov. 22, 2004, the content of which are incorporated herein by reference in its entirety.

Throughout this application, several publications are referenced herein by Arabic numerals with parentheses. Full citations for the references referenced by Arabic numerals with parentheses may be found at the end of the specification immediately preceding the claims. Disclosure of these references in their entirety is hereby are incorporated by reference into this application to more fully describe the state of the art to which the present invention pertains.

FIELD OF THE INVENTION

The present invention relates to locating and targeting critical portions or sites on the spike protein ("S protein") of the SARS-associated coronavirus ("SARS-CoV") responsible for the viral infection which causes Severe Acute Respiratory Syndrome ("SARS"). The present invention also relates to new synthetic peptides for the prevention and treatment of SARS. The present invention further relates to testing antiviral activity exerted by antiviral agents using real-time quantitative PCR.

BACKGROUND OF THE INVENTION

SARS spread to over thirty countries in 2003. There were more than 8,000 individuals infected and 800 lives were lost. A novel SARS-CoV was subsequently identified as the etiological agent of SARS (1-3), and it was further confirmed that the virus caused a similar disease in cynomolgus macaques (4). Although SARS appears to have been successfully contained, re-emergence of this life threatening disease remains a significant possibility. There have been three laboratory-acquired and four community-acquired SARS cases were recently reported in Singapore, Taiwan and China (40). Therefore, effective vaccines or antiviral drugs against this disease are urgently needed.

SARS-CoV-like viruses have been isolated from and characterized in small mammals such as civet cats and raccoon dogs, implying that these animals may be the source of SARS (5). Important factors associated with the emergence of novel infectious diseases from animal sources include extensive exposure and rapid virus evolution (6). Phylogenetic analysis has revealed that although human SARS-CoV and animal SARS CoV-like viruses are related to the three groups of the previously found coronaviruses, they are different enough to make up their own, the fourth group, which may be a big family in wildlife. Increasing consumer demands for wild/farmed animals in Guangdong, China in the past 15 years has provided an incubator to facilitate interspecies virus transmission from wild/farmed animals to domestic animals and humans. The mutation rate will increase in interspecies transmitted viruses due to novel selection pressure in the new hosts.

In SARS-CoV infection, the spike protein ("S protein") recognizes and binds to host cell receptors, and the conformational changes induced in the S protein would then facilitate the fusion between the viral envelope and host cell membranes. Previous studies have clearly identified that there are significant sequence variations in the region encoding the S protein, with twelve notable amino acid substitution changes (5). These substitutions may hold the key to understanding why and how the virus crossed the species barrier from animals to humans in the recent outbreak. The rapid mutation of these sites was further elucidated in a recent study for SARS surveillance. By comparing animal SARS-CoV-like viruses isolated in May 2003 (5) and those isolated after October 2003 (unpublished data), further variations in these sites are identified, which are completely identical to the human SARS-CoV isolated from a patient in December 2003 in Guangzhou (7) (Table 1). The rapid mutations in these sides suggest that at least some of these mutations would play a crucial role in viral transmission across the species barrier from animals to humans. It is hypothesized that agents that interfered with, or bound competitively with these protein domains would be able to inhibit SARS-CoV infections by disrupting the function of the S protein. To test this hypothesis, ten peptides that spanned these variable regions were synthesized and their antiviral effects in a cell culture system were investigated.

TABLE 1

Amino Acid Variation of S Protein Between Animals and Human SARS-CoV

| Sampling | Viruses | P1 227 | P2 239 | P3 261 | P4 360 | P5 497 | P6 558 | P7 607 | P8 701 | P8 743 | P8 754 | P9 894 | P10 1163 |
|---|---|---|---|---|---|---|---|---|---|---|---|---|---|
| Animal (May 2003) (5) | SZ1 | K | L | K | S | K | I | P | L | A | V | A | E |
| | SZ3 | K | L | K | S | K | F | P | L | A | V | A | E |
| | SZ16 | K | L | K | S | K | I | P | L | A | V | A | E |
| Animal (October 2003)* | Hc/SZ/266/03 | N | S | T | S | N | F | S | S | R | A | T | E |
| Animal (November 2003)* | Hc/SZ/DM1/03 | N | S | T | S | N | F | S | S | R | A | T | E |
| Animal (December 2003)* | Hc/GZ/32/03 | N | S | T | S | R | F | S | S | R | A | T | E |
| | Hc/GZ/81/03 | N | S | T | S | N | F | S | S | R | A | T | E |
| | Hc/SZ/61/03 | K | S | T | S | R | F | S | S | R | A | T | E |
| | Hc/SZ/79/03 | N | S | T | S | R | F | S | S | R | A | T | E |
| | CFb/SZ/94/03 | N | S | T | S | R | F | S | S | R | A | T | E |
| Human (December 2003) (7) | Hu/Gz/1/04 | N | S | T | S | N | F | S | S | R | A | T | E |
| Human (February 2003) (13) | GZ01 | N | L | T | F | N | F | S | S | T | A | T | K |

TABLE 1-continued

Amino Acid Variation of S Protein Between Animals and Human SARS-CoV

| Sampling | Viruses | P1 227 | P2 239 | P3 261 | P4 360 | P5 497 | P6 558 | P7 607 | P8 701 | P8 743 | P9 754 | P10 894 | 1163 |
|---|---|---|---|---|---|---|---|---|---|---|---|---|---|
| | GZ43 | N | L | T | F | N | F | S | S | T | A | T | K |
| | GZ50 | N | S | T | F | N | F | S | S | T | A | T | K |
| | GZ60 | N | L | T | F | N | F | S | S | T | A | T | K |

*Unpublished data.
Abbreviations used:
Human ("Hu");
Himalayan civet ("Hc");
Chinese ferret-badger ("CFb"),
Guangzhou ("GZ"); and
Shenzhen ("SZ").
P1-P10 are SEQ ID NOs.: 1-10, respectively.

Antiviral peptides targeting HIV-1 (8, 9), gp40 of feline immunodeficiency virus (FIV) (10), and the coiled-coil domain of human T-cell leukemia virus type-1 (HTLV-1) (11) have been demonstrated to be effective inhibitors of these viral infections, with potential therapeutic value in the treatment of the viral diseases. The inhibitory effects of these synthetic peptides were mediated by blocking the interaction of viral proteins with their cellular receptors, or alternatively, by preventing membrane fusion. Based on these findings, a recent study has demonstrated that a peptide targeting the heptad repeat 2 region of the SARS-CoV S protein inhibits virus infection in the micromolar range (12).

In this invention, peptides which target four regions of the S protein were synthesized and identified to effectively inhibit SARS CoV infection in a monkey kidney (FRhK-4) cell line. Synergistic antiviral effects were observed when cells were treated with combinations of two or three of these peptides prior to infection. 3D modeling indicated that three of the antiviral peptides map to subunit interfaces putatively crucial for the correct assembly of the trimeric peplomer. The results suggest a novel inhibitory mechanism distinct from the previously reported anti-SARS-CoV peptide, which disrupted the heptad repeat 1-heptad repeat 2 ("HR1-HR2") interaction.

Definitions

"Peplomers" described herein means layers of protein which surround the capsid in animal viruses with tubular nucleocapsids. The envelope has an inner layer of lipids and virus specified proteins also called membrane or matrix proteins. The outer layer has one or more types of morphological subunits called peplomers which project from the viral envelope; this layer always is composed of glycoproteins.

"Subject" shall mean any animal, such as a mammal or a bird, including, without limitation, a cow, a horse, a sheep, a pig, a dog, a cat, a rodent such as a mouse or rat, a turkey, a chicken and a primate. In the preferred embodiment, the subject is a human being.

"Pharmaceutically acceptable carrier" shall mean any of the various vehicles or carriers known to those skilled in the art. For example, pharmaceutically acceptable carrier includes, but is not limited to, 0.01-0.1 M and preferably 0.05 M phosphate buffer or 0.8% saline. Additionally, such pharmaceutically acceptable carriers can be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions and suspensions, including saline and buffered media. Parenteral vehicles include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, chelating agents, inert gases, and the like.

Peptides described herein are represented by "one-letter symbols" for amino acid residues as follows:

| A | Ala | Alanine |
|---|---|---|
| R | Arg | Arginine |
| N | Asn | Asparagine |
| D | Asp | Aspartic acid |
| B | Asx | Asn or Asp |
| C | Cys | Cysteine |
| Q | Gln | Glutamine |
| E | Glu | Glutamic acid |
| Z | Glx | Gln or Glu |
| G | Gly | Glycine |
| H | His | Histidine |
| I | Ile | Isoleucine |
| L | Leu | Leucine |
| K | Lys | Lysine |
| M | Met | Methionine |
| F | Phe | Phenylalanine |
| P | Pro | Proline |
| S | Ser | Serine |
| T | Thr | Threonine |
| W | Trp | Tryptophan |
| Y | Tyr | Tyrosine |
| V | Val | Valine |

SUMMARY OF THE INVENTION

It is an object of this invention to develop agents to interfere with, or bind competitively with the variation sites on the S protein of SARS-CoV. Another object of this invention to identify regions of the S protein of SARS-CoV that is important for peplomer function using these agents. Yet another object of this invention is the use of these agents to inhibit SARS-CoV infection by disrupting the function of the S protein. The agents described herein are 20 mer peptides designed to span the twelve identified variations of the S gene based on the genome sequences between human SARS-CoV and animal SARS-CoV-like virus isolates. The peptides of this invention are represented by the following formulas (SEQ ID NO.:1-10):

| | |
|---|---|
| X-FKLPLGINITNFRAILTAFS-Z; | SEQ ID NO.:1 |
| X-PTTFMLKYDENGTITDAVDC-Z; | SEQ ID NO.:2 |
| X-VLYNSTFFSTFKCYGVSATK-Z; | SEQ ID NO.:3 |
| X-PALNCYWPLNDYGFYTTSGI-Z; | SEQ ID NO.:4 |
| X-RDVSDFTDSVRDPKTSEILD-Z; | SEQ ID NO.:5 |
| X-YQDVNCTDVSTAIHADQLTP-Z; | SEQ ID NO.:6 |
| X-SNNTIAIPTNFSISITTEVM-Z; | SEQ ID NO.:7 |
| X-QYGSFCTQLNRALSGIAAEQ-Z; | SEQ ID NO.:8 |
| X-GIGVTQNVLYENQKQIANQF-Z; | SEQ ID NO.:9 |
| and | |
| X-IQKEIDRLNEVAKNLNESLI-Z. | SEQ ID NO.:10 | in which amino acid residues are represented by the one-letter symbols, wherein X is an amino group, an acetyl group, a 9-fluorenylmethoxy-carbonyl group, or a hydrophobic group, and Z is a carboxyl group, an amido group, or a hydrophobic group.

The invention provides a method for locating sites of SARS-CoV S protein responsible for causing viral infection in a cell comprising contacting the cell prior to SARS-CoV infection with a peptide having the formula: X-PTTFMLKY-DENGTITDAVDC-Z (SEQ ID NO.:2); X-YQDVNCTD-VSTAIHADQLTP-Z (SEQ ID NO.:6); X-QYGSFCTQLN-RALSGIAAEQ-Z (SEQ ID NO.:8); X-IQKEIDRLNEVAKNLNESLI-Z (SEQ ID NO.:10), or a combination thereof.

The invention further provides a method for preventing or inhibiting SARS-CoV infection in a subject comprising administering to the subject an effective amount of a pharmaceutical composition comprising SEQ ID NO.:2, SEQ ID NO.:6, SEQ ID NO.:8, SEQ ID NO.:10, or a combination thereof, and a pharmaceutically acceptable carrier.

The invention also provides a method of testing antiviral activity exerted by antiviral agents using real-time quantitative PCR with a specific forward primer, reverse primer, and a fluorescence-labeled probe.

BRIEF DESCRIPTION OF THE DRAWINGS

The patent or application file contains at least one drawing executed in color. Copies of this patent or patent application publication with color drawings will be provided by the Office upon request and payment of the necessary fee.

The foregoing and additional features and advantages of the present invention will be better understood in light of the accompanying "Detailed Description Of The Invention" and the drawings described in this section.

FIG. 1 Diagram of SARS-Co V Genome and Locations of the Synthetic Peptides

The S protein of SARS-CoV includes of 1255 amino acid residues. Ten peptides (P1-P10 (SEQ ID NOs.:16-25, respectively)) were designed to block viral entry based on the hypothesis that the residue variations between human SARS-CoV and animal SARS-CoV-like viruses might determine the preference of viral infection between human and animals. Amino acid variation(s) in each peptide are highlighted by italics and the alternative amino acid(s) identified from animal SARS-CoV-like virus is shown in Table 1. The arrows indicate the location of each peptide in the S protein. Peptides with strong anti-SARS-CoV activities are shown in SEQ ID NO:17 ("P2"), SEQ ID NO.:21 ("P6"), SEQ ID NO:23 ("P8") and SEQ ID NO.:25 ("P10"). Abbreviations used: angiotensin-converting enzyme 2 binding region ("ACE2"); heptad repeats ("HR1" and "HR2"); open reading frame ("ORF"); and trans-membrane domain ("T"). Results of ELM and coiled-coil prediction analysis are also listed.

FIGS. 2A-2F Peptide-Mediated Antiviral Effects Determined by Cytopathic Effects of SARS-CoV Infection FRhK-4 cells were incubated with (FIGS. 2A, 2C, 2D and 2F) or without peptides (FIGS. 2B and 2E) for one hour before viral infection. Thirty-six hours post-infection, photos were taken to show cell morphology using phase-contrast microscopy (FIGS. 2A-2D, 400×) or virus morphology using electron microscopy (FIGS. 2E and 2F). The cells were incubated with peptides and did not show cytotoxic effect (FIG. 2A), while the untreated cells showed typical CPE after infection with SARS-CoV (FIG. 2B). No visible CPE appeared when the cells were treated with SEQ ID:8 at 50 μg/ml (FIG. 2C), or CPE was significantly reduced by the treatment of SEQ ID:8 at 25 μg/ml (FIG. 2D). Electron microscopy shows typical morphology of SARS-CoV (highlighted by arrows) within the infected cell (FIG. 2E), compared to an absence of virus visible in the cells protected by SEQ ID NO.:8 at 100 μg/ml (FIG. 2F).

Figure 3A:
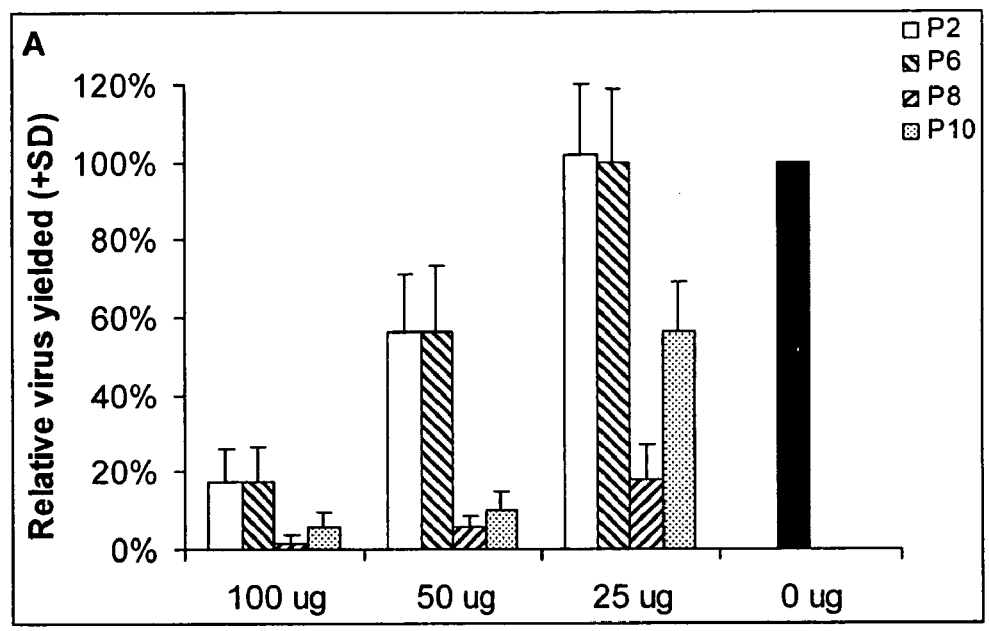
Figure 3B:
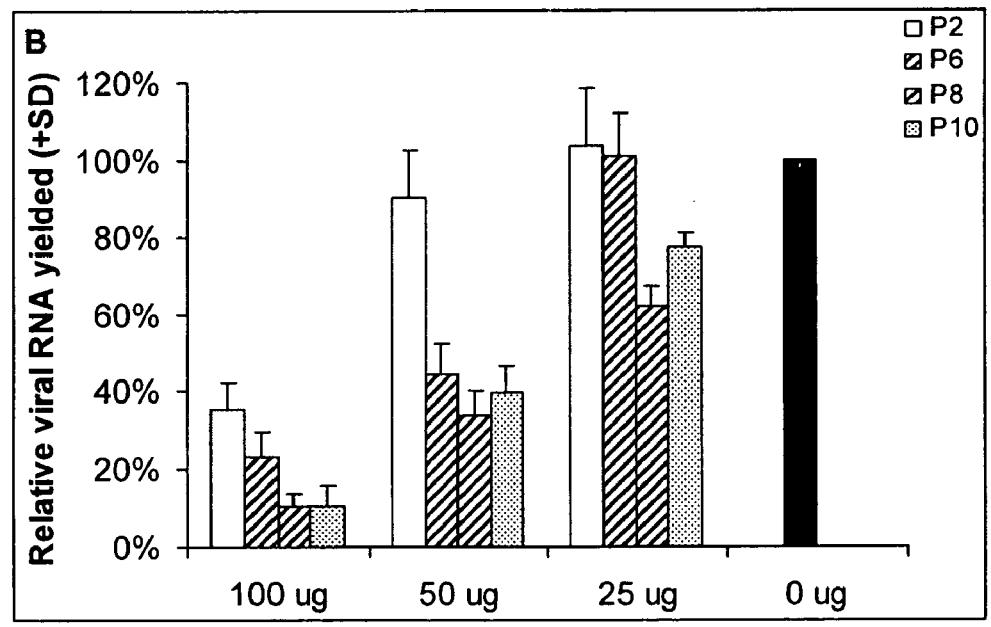

FIGS. 3A and 3B Antiviral Effects Determined Mediated by Single Effective Peptide The antiviral activities of the effective peptides SEQ ID NO.:2, SEQ ID NO.:6, SEQ ID NO.:8 and SEQ ID NO.:10 were determined by measuring the viral titers in the culture media (FIG. 3A) and viral RNA copies in the cells (FIG. 3B). FRhK-4 cells were pre-incubated with different concentrations of peptides (i.e., 100 μg/ml, 50 μg/ml and 25 μg/ml, respectively). Thirty-six hours post-infection, relative virus yielded in the culture media was titrated by $TCID_{50}$ and compared between peptide pretreated and non-pretreated groups (FIG. 3A); relative viral genome copies in the cells were determined by real-time quantitative RT-PCR in triplicates and the standard deviations were illustrated (FIG. 3B). The relative viral titres or RNA copies of control were defined as 100%. The experiments were repeated at least twice.

Figure 4:
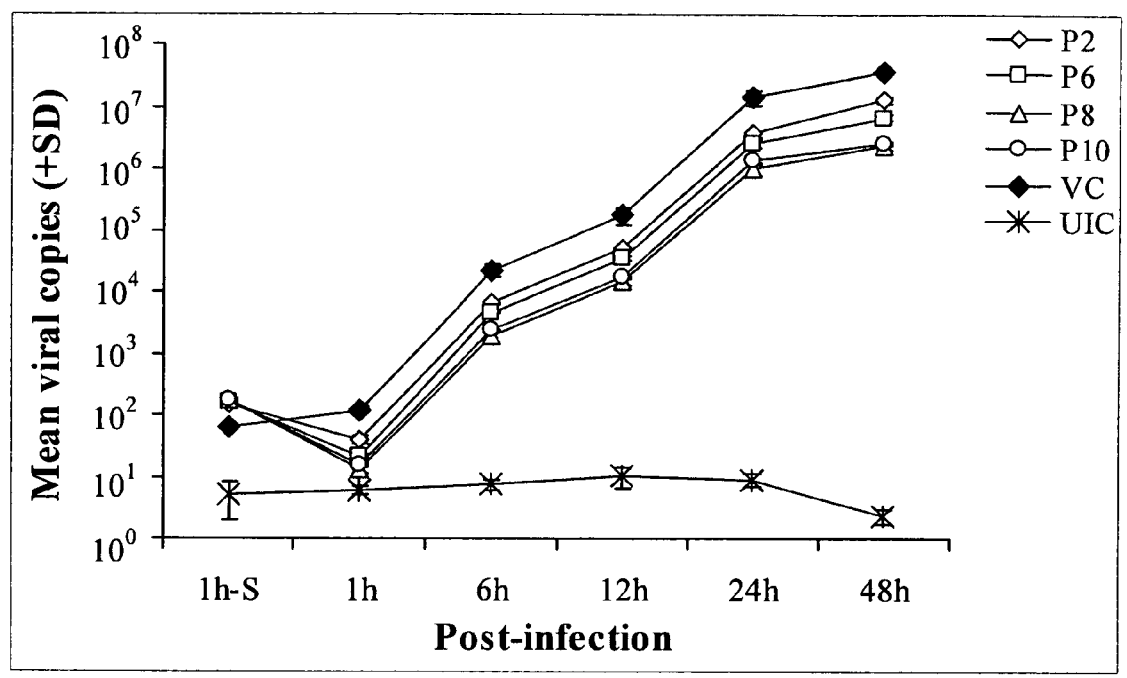

FIG. 4 Active Peptides Inhibit Virus Entry of the Cells

Copies of the viral RNA were determined by Q-RT-PCR at different time points post-infection as indicated. Cells untreated by peptides, designed as virus controls ("VC"), were infected with the same dose of virus as the others. The uninfected cells (labelled as "UIC") were treated with SEQ ID NO.:8 and used as negative controls.

Figure 5A:
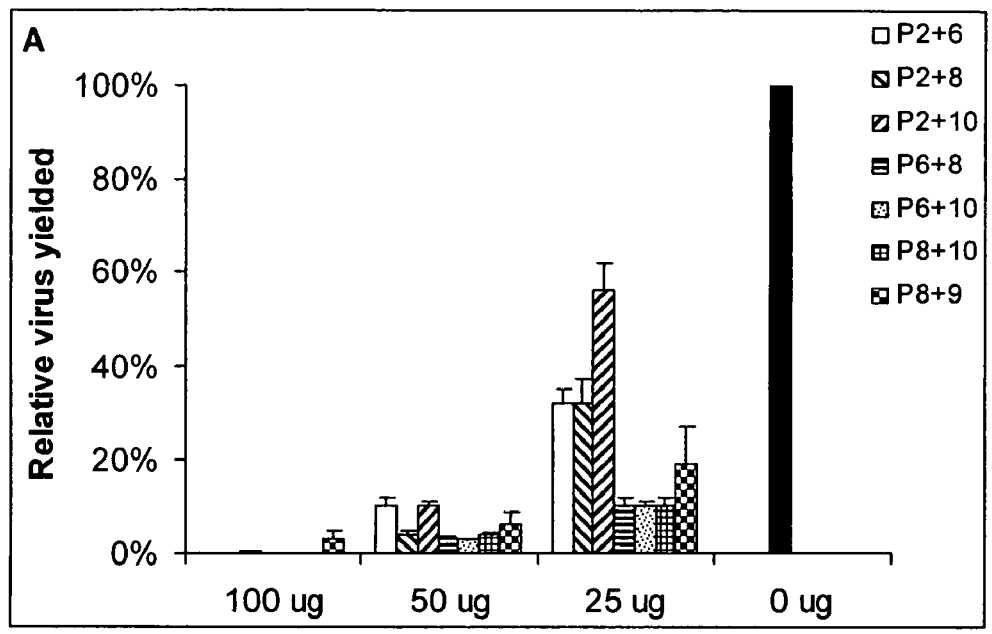
Figure 5B:
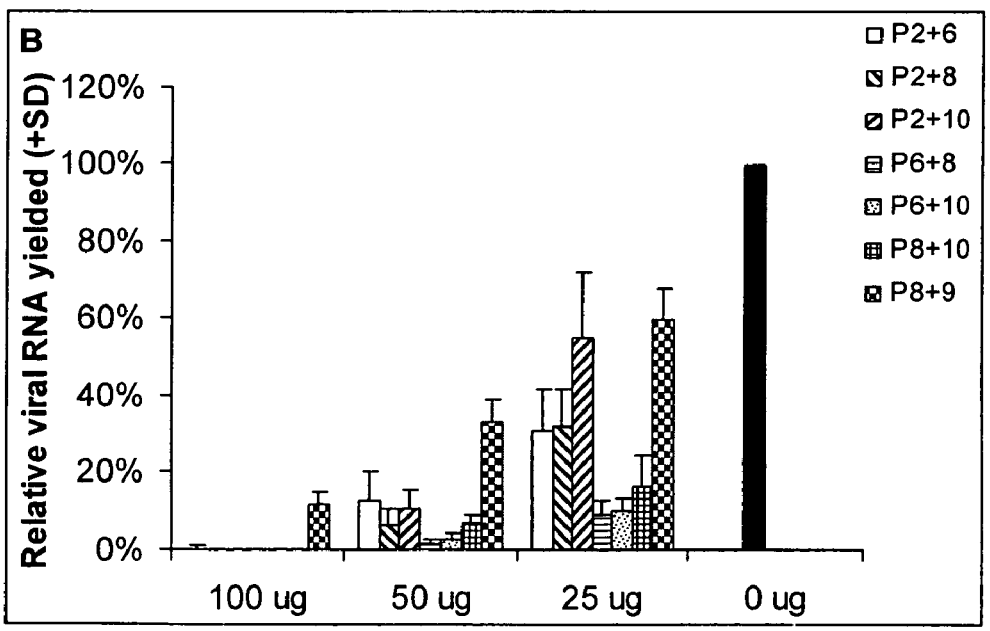

FIGS. 5A and 5B Synergistic Antiviral Effects Mediated by Combining Two Active Peptides FRhK-4 cells were incubated with different concentrations of two-peptide mixtures for one hour before viral infection. In each experiment, equal amount (by weight) of two peptides were mixed, and the final concentration of total peptides used were 100 μg/ml, 50 μg/ml, and 25 μg/ml, respectively. A combination of non-active peptide SEQ ID NO:9 and active SEQ ID NO:8 was used as a control. The antiviral effects were determined by titration of the yielded virus in culture media (FIG. 5A) and measuring intracellular viral RNA copies (FIG. 5B) as described in FIGS. 3A and 3B.

Figure 6A:
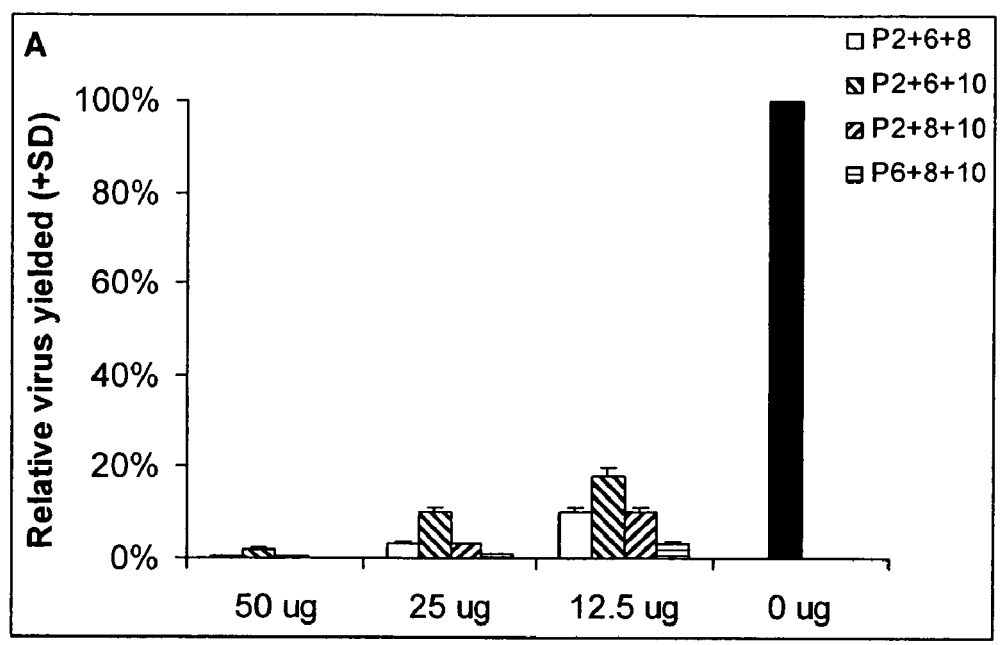
Figure 6B:
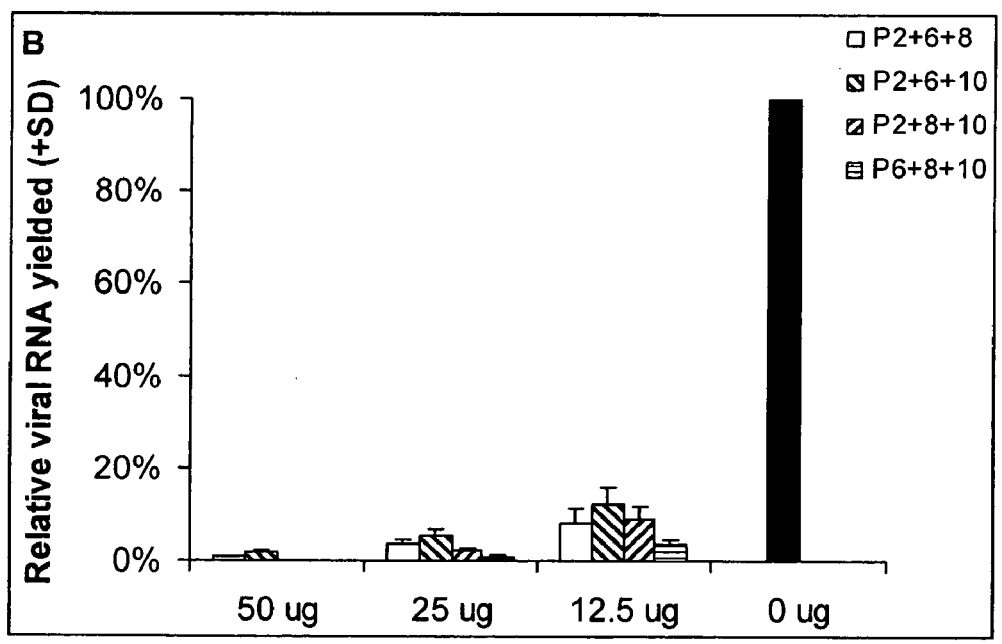

FIGS. 6A and 6B Synergistic Antiviral Effects Mediated by Combination of Three Effective Peptides FRhK-4 cells were incubated with different concentrations of three-peptide mixtures for one hour before SARS-CoV infection. In each experiment, equal amount (by weight) of three peptides were used, and the final concentrations of total peptides used are indicated in FIGS. 6A and 6B. Synergistic antiviral effects were determined by titration of the released virus in culture media (FIG. 6A) and measuring intracellular viral RNA copies (FIG. 6B) as described in FIGS. 3A and 3B.

Figure 7A:
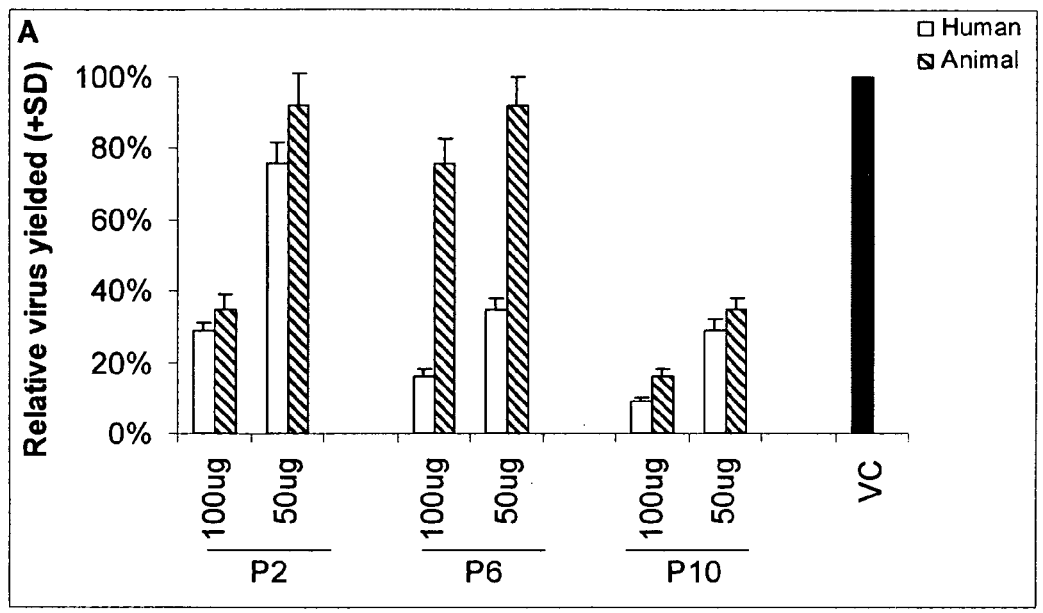
Figure 7B:
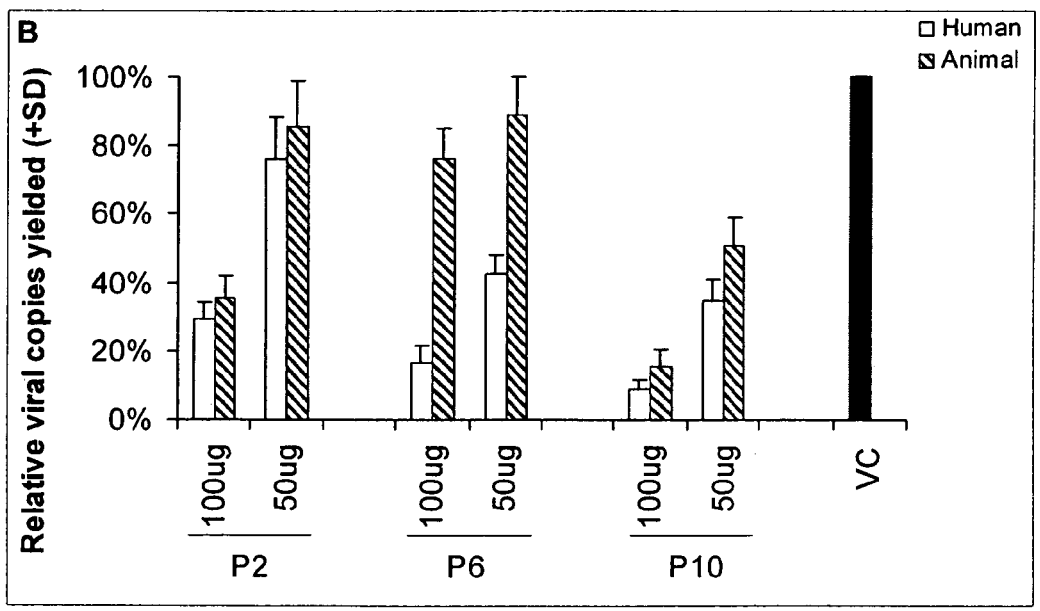

FIGS. 7A and 7B Comparison of Anti-Human Virus Effects Between Human Virus-Derived Peptides and Animal Virus-Derived Peptides FRhK-4 cells were incubated with 100 and 50 μg of human or animal virus-derived peptides for one hour before SARS-CoV infection. The antiviral effects were evaluated by titration of the released virus in culture media (FIG. 7A) and measuring intracellular viral RNA copies (FIG. 7B) as described in FIGS. 3A and 3B. Abbreviations used: virus controls ("VC").

FIGS. 8A-8F Modelling of the Peptide Location

Figure 8F:
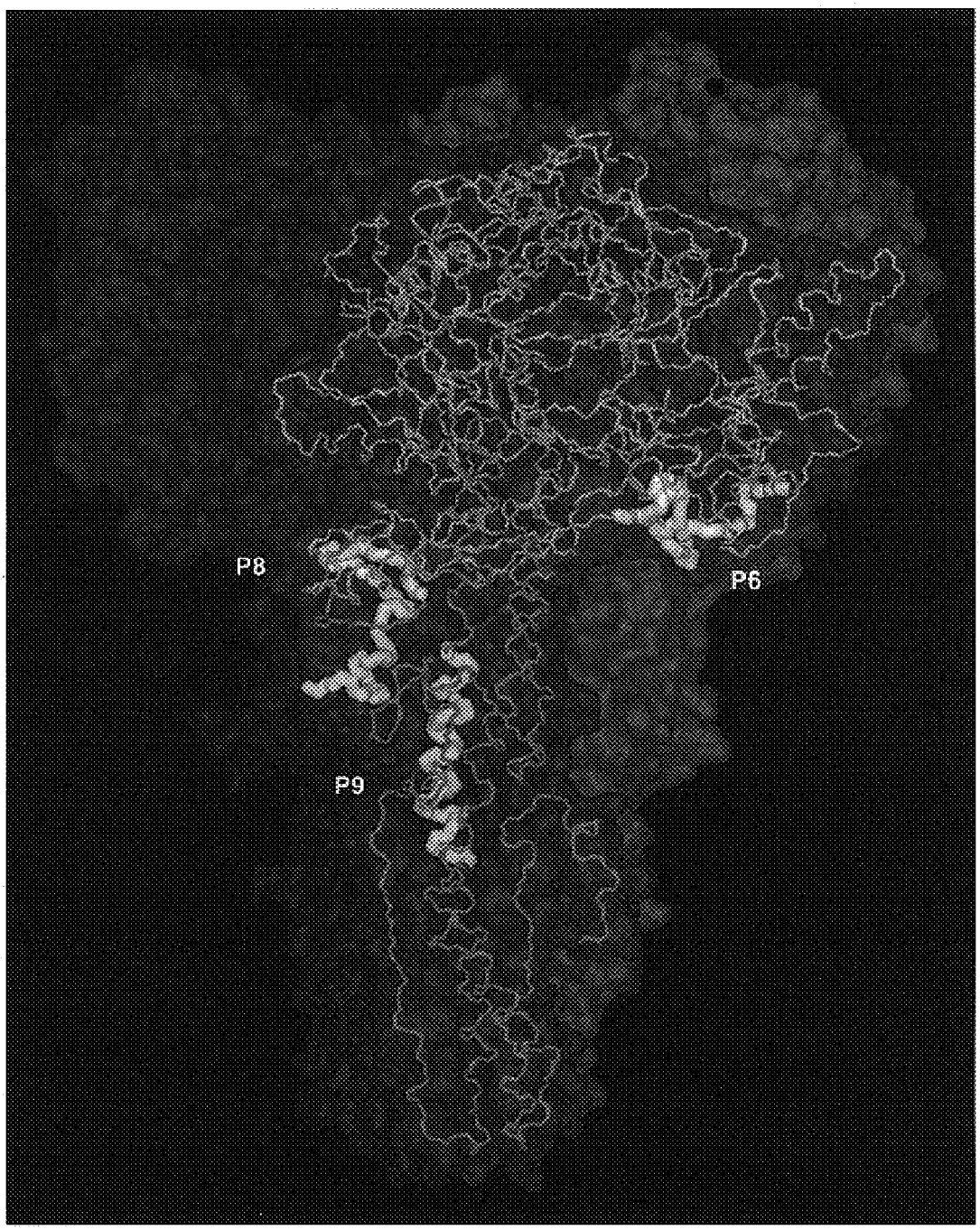

FIG. 8A shows a ribbon representation of S1 and S2 subunits: eight peptides are shown with different colors in the 1-1020 modelled regions; SEQ ID NO.: 10 ("P10") is in a globular domain, corresponding to the 1021-1195 region, which as been separately modelled. FIGS. 8B-8E show enlarged views of the four S glycoprotein segments which correspond to the active peptides SEQ ID NO.:2 ("P2"), SEQ ID NO.:6 ("P6"), SEQ ID NO.:8 ("P8") and SEQ ID NO.:10 ("P 10"), respectively, and are also shown in the same colors. SEQ ID NO.:7 cannot be shown since it is outside the modelled region. FIG. 8F shows the backbone of one of the monomers is highlighted with orange and green for S1 and S2, respectively. The positions of SEQ ID NO.:6 ("P6"), SEQ ID NO.:8 ("P8"), and SEQ ID NO.:9 ("P9") are highlighted with thick threads.

Figure 9A:
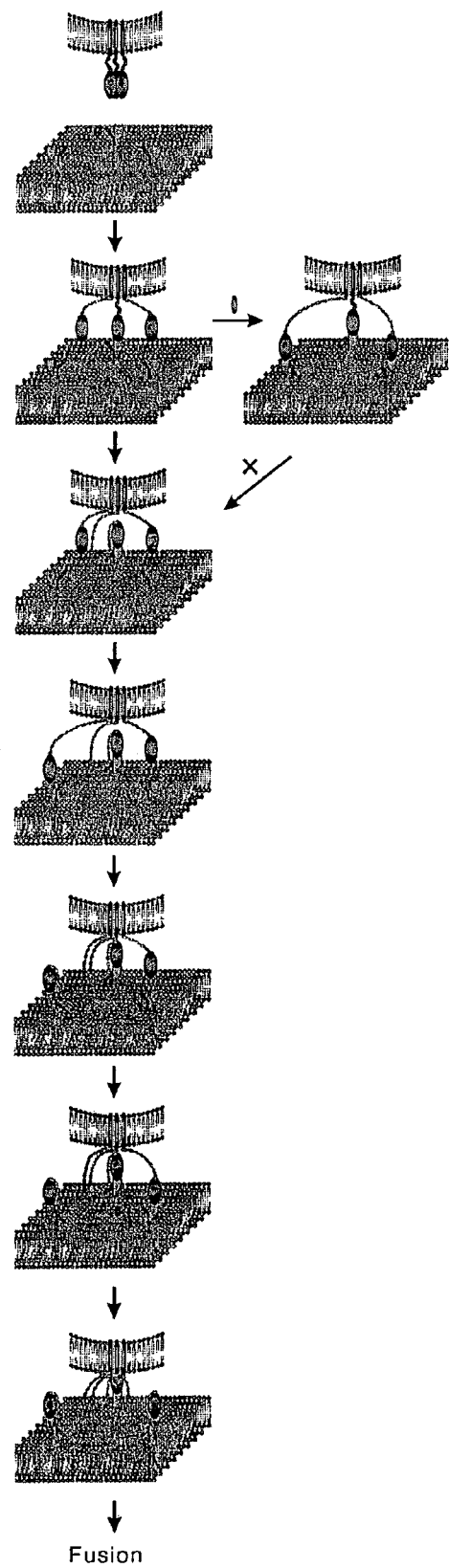
Figure 9B:
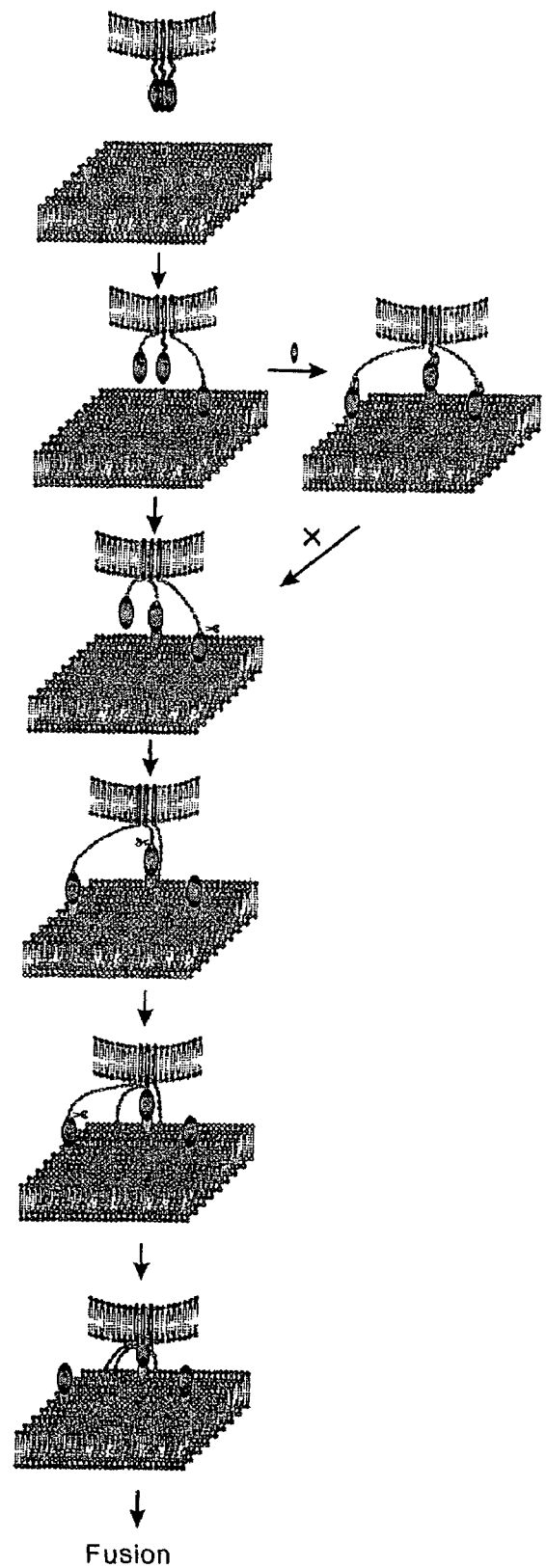
Figure 9C:
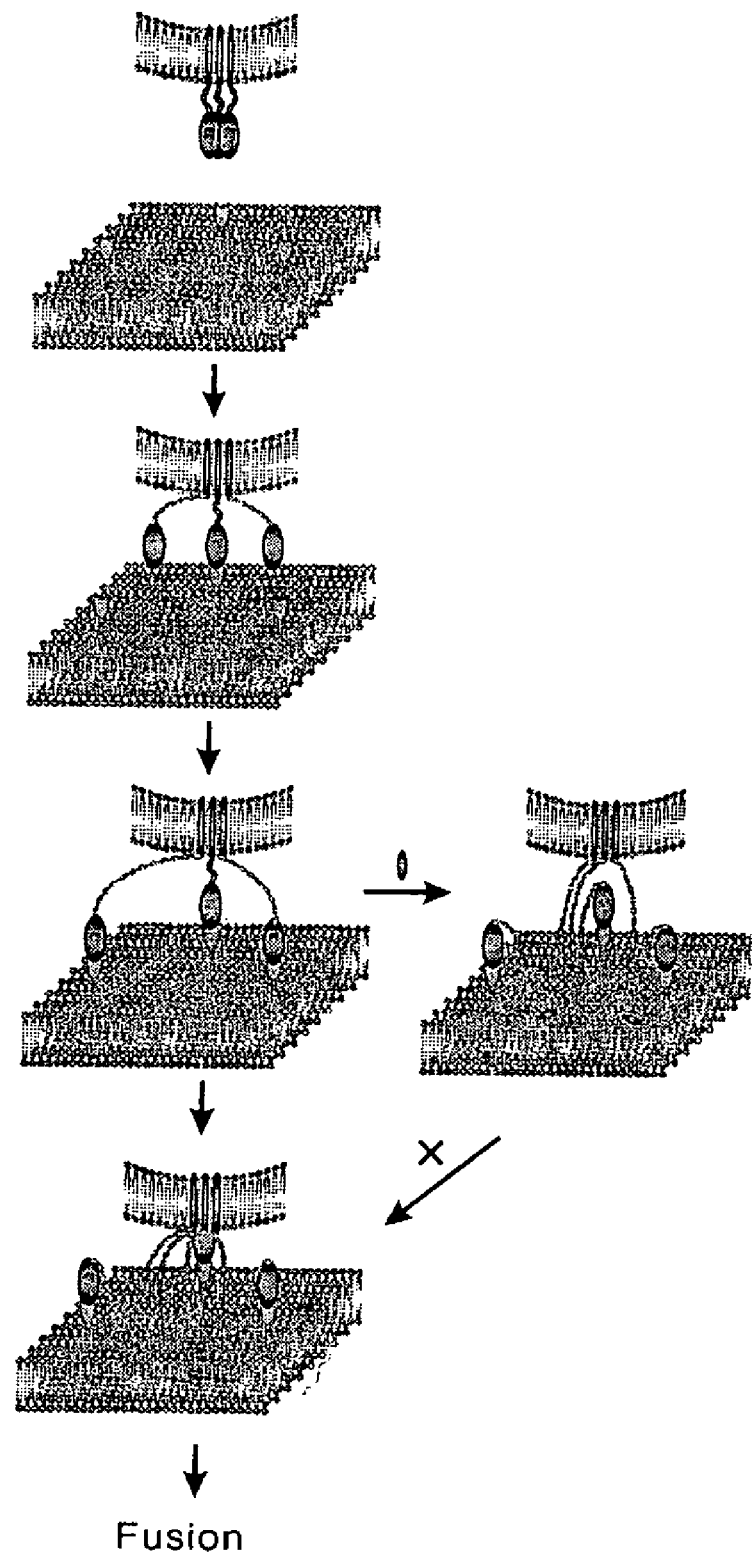

FIGS. 9A-9C Proposed Model of Peptide Inhibition

FIG. 9A shows an unidentified co-receptor is required for SARS-CoV to enter the host cells. The synthetic peptide may block the viral entry by binding to the co-receptor. FIG. 9B shows that after binding to the receptor (ACE2), the proteolytic site in each S protein monomer is exposed. An unidentified protease then processes the S protein into S1 and S2 domains, which triggers conformation change and membrane fusion. The inhibitory peptides may bind to the S protein monomer and block the action of the protease. FIG. 9C shows a conformation change is required for the insertion of the viral peplomer into the host membrane before the fusion step. The synthetic peptides may bind to the peplomer and alter its conformation necessary for viral entry.

DETAILED DESCRIPTION OF THE INVENTION

Described herein are peptides that exhibit potent antiviral activity. These peptides include SEQ ID NO.:2, SEQ ID NO.:6, SEQ ID NO.:8, and SEQ ID NO.:10, are targeted to specific sites on the S protein of SARS-CoV responsible for viral infection. Also described herein are assays for testing the antiviral activity of such peptides. Finally, the invention involves the use of these peptides or other synthetic peptides targeted to the described critical sites as inhibitors of SARS-CoV infection in the treatment of SARS.

This invention provides insight into the important functional regions of the SARS-CoV S protein and provides treatments based upon prevention or inhibition of SARS-CoV infection. Angiotensin-converting enzyme 2 ("ACE2") has been reported to be a receptor of SARS-CoV and the region of the S protein that binds to ACE2 has been elucidated (23, 24, 27, 33). It was also demonstrated that interaction of HR1 and HR2 is important for the fusion of virus envelope and host cell membrane (12). However, the other functional regions in the S protein associated with viral infection are not yet defined.

In another embodiment, the critical regions of the S protein were probed using ten peptides, i.e., SEQ ID NOs:1-10, that were designed based on the hypothesis that the rapid mutation sites on the S protein may play a crucial role in crossing the species barrier from animals to humans.

The ten peptides were designed to span the 12 identified variations of the S gene based on genome sequences between human SARS-CoV and animal CoV-like virus isolates (5). The peptides were designed with incorporation of ELM and coiled-coil prediction analysis (FIG. 1). It has been demonstrated that the S1 domain (residues 12-672) is responsible for receptor binding (23, 24), and the S2 domain (residues 673-1255) is involved in virus-host cell fusion (25, 26). Sequence alignment of the human and animal viruses showed that there are seven variations occurred in the S1 domain and five variations in the S2 domain (Table 1 and FIG. 1). All these variations in the design of antiviral peptides were covered with six peptides, i.e., SEQ ID NOs.:1-6, targeting the S1 region and four peptides targeting the S2 region, i.e., SEQ ID NOs.:7-10. Variations F360S and N479K (human to animal) located in the identified virus receptor (angiotensin-converting enzyme 2, ACE2) binding region (23, 27) were covered by peptides SEQ ID NOs.:3 and 4. Peptide 8 and peptide SEQ ID NO.:10, which covered variations T894A and K1163E, respectively located in the heptad repeat 1 ("HR1", residues 892-1013) and 2 regions ("HR2", residues 1153-1198) of the viral S protein (12). The other 6 peptides were derived from undefined regions (FIG. 1).

The peptides of this invention were synthesized by Invitrogen (Carlsbad, Calif., USA). The sequences are as follows (SEQ ID NOs.:1-10):

| | |
|---|---|
| X-FKLPLGINITNFRAILTAFS-Z | SEQ ID NO.:1 |
| X-PTTFMLKYDENGTITDAVDC-Z | SEQ ID NO.:2 |
| X-VLYNSTFFSTFKCYGVSATK-Z | SEQ ID NO.:3 |
| X-PALNCYWPLNDYGFYTTSGI-Z | SEQ ID NO.:4 |
| X-RDVSDFTDSVRDPKTSEILD-Z | SEQ ID NO.:5 |
| X-YQDVNCTDVSTAIHADQLTP-Z | SEQ ID NO.:6 |
| X-SNNTIAIPTNFSISITTEVM-Z | SEQ ID NO.:7 |
| X-QYGSFCTQLNRALSGIAAEQ-Z | SEQ ID NO.:8 |
| X-GIGVTQNVLYENQKQIANQF-Z | SEQ ID NO.:9 |
| X-IQKEIDRLNEVAKNLNESLI-Z | SEQ ID NO.:10 |

This invention provides a method for locating sites of SARS-CoV S protein responsible for causing viral infection in a cell comprising contacting the cell prior to SARS-CoV infection with a peptide having the formula: X-PTTFMLKY-DENGTITDAVDC-Z (SEQ ID NO.:2), X-YQDVNCTD-VSTAIHADQLTP-Z (SEQ ID NO.:6), X-QYGSFCTQLN-RALSGIAAEQ-Z (SEQ ID NO.:8), X-IQKEIDRLNEVAKNLNESLI-Z (SEQ ID NO.:10), or a combination thereof. The peptide can be a combination of two peptides (e.g., SEQ ID NO:6+SEQ ID NO:8). The peptide may be positioned at SARS-CoV S protein amino acid residue 259-278, amino acid residue 598-617, amino acid residue 737-756, or amino acid residue 1161-1180. The peptide binds either on or adjacent to the ACE2 binding region or the S1 and S2 domains of SARS-CoV S glycoprotein. In this way, the peptide helps to prevent, inhibits, or reduce SARS-CoV infection.

In the method above, the cell may be from a primate, a monkey cell line (e.g., FRhK-4 and VeroE6), a human, or a human cell line (e.g., Caco2, Huh7, CNE1 and CNE2).

In one embodiment, the peptide is SEQ ID NO.:2 and interferes with ACE2 binding site conformation change.

In another embodiment, the peptide is SEQ ID NO.:2, SEQ ID NO.:6, SEQ ID NO.:8, or SEQ ID NO.: 10, and the peptide interferes with peplomer function by competitive binding to an S protein monomer by mimicking regions exposed after ACE2-binding induced conformation change. The affected sites are preferably S protein amino acid residues 259-278, 598-617, 737-756, or 1161-1180.

The invention also provides a method for preventing or inhibiting SARS-CoV infection in a subject comprising administering to the subject an effective amount of a pharmaceutical composition comprising SEQ ID NO.:2, SEQ ID NO.:6, SEQ ID NO.:8, SEQ ID NO.:10, or a combination thereof, and a pharmaceutically effective carrier. The pharmaceutical composition may comprise a single peptide (e.g., SEQ ID NO:8), a dual peptide (e.g., SEQ ID NO:6+SEQ ID NO:8), or a combination thereof. In the preferred embodiment, the subject is a human being.

The following delivery systems, which employ a number of routinely used pharmaceutical acceptable carriers, are only representative of the many embodiments envisioned for administering the above pharmaceutical compositions.

Injectable drug delivery systems include solutions, suspensions, gels, microspheres and polymeric injectables, and can comprise excipients such as solubility-altering agents (e.g., ethanol, propylene glycol, and sucrose) and polymers (e.g., polycaprylactones and PLGA's). Implantable systems include rods and discs, and can contain excipients such as PLGA and polycaprylactone.

Oral delivery systems include tablets and capsules. These can contain excipients such as binders (e.g., hydroxypropylmethylcellulose, polyvinyl pyrilodone, other cellulosic materials, and starch), diluents (e.g., lactose and other sugars, starch, dicalcium phosphate, and cellulosic materials), disintegrating agents (e.g., starch polymers and cellulosic materials) and lubricating agents (e.g., stearates and talc).

Transmucosal delivery systems include patches, tablets, suppositories, pessaries, gels, and creams, and can contain excipients such as solubilizers and enhancers (e.g., propylene glycol, bile salts, and amino acids), and other vehicles (e.g., polyethylene glycol, fatty acid esters, and derivatives, and hydrophilic polymers such as hydroxypropylmethylcellulose and hyaluronic acid).

Dermal delivery systems include, for example, aqueous and nonaqueous gels, creams, multiple emulsions, microemulsions, liposomes, ointments, aqueous and nonaqueous solutions, lotions, aerosols, hydrocarbon bases, and powders, and can contain excipients such as solubilizers, permeation enhancers (e.g., fatty acids, fatty acid esters, fatty alcohols and amino acids), and hydrophilic polymers (e.g., polycarbophil and polyvinylpyrolidone). In one embodiment, the pharmaceutically acceptable carrier is a liposome or a transdermal enhancer.

Solutions, suspensions and powders for reconstitutable delivery systems include vehicles such as suspending agents (e.g., gums, zanthans, cellulosics, and sugars), humectants (e.g., sorbitol), solubilizers (e.g., ethanol, water, PEG, and propylene glycol), surfactants (e.g., sodium lauryl sulfate, Spans, Tweens, and cetyl pyridine), preservatives and antioxidants (e.g., parabens, vitamins E and C, and ascorbic acid), anti-caking agents, coating agents, and chelating agents (e.g., EDTA).

The invention further provides a method of testing antiviral activity exerted by antiviral agents using real-time quantitative PCR with a specific forward primer, reverse primer, and a fluorescent-labeled probe. The forward primer can be a fragment of the DNA sequence of the SARS-CoV S protein gene, such as 5'-GCTTAGGCCCTTTGAGAGAGACA-3' (SEQ ID NO.:11). The reverse primer can be a fragment of the DNA sequence of the SARS-CoV S protein gene, such as 5'-GCCAATGCCAGTAGTGGTGTAAA-3' (SEQ ID NO.: 12)). The fluorescent-labeled probe, such as 5'-CCTGATG-GCAAACCTTGCAC-3' (SEQ ID NO.:13), can also be labeled by any fluorescence as reporter in any real-time PCR detection system such as 5'-(TET)CTAATGTGCCTTTCTC-CCCTGATGGCA(TAMRA)-3' (SEQ ID NO.:14). In addition to the specific forward primer, reverse primer, and the fluorescent-labeled probe, a phosphate probe, such as 5'-(LC640)CACCTGCTCTTAATTGTTATTGGCC-3' (SEQ ID NO.:15), can also be used to test antiviral activity exerted by antiviral agents using real-time quantitative PCR.

The present invention will be better understood from the "Experimental Section" that follows. However, one skilled in the art will readily appreciate that the specific methods and results discussed are merely illustrative of the present invention as described more fully in the claims which follow thereafter.

Experimental Section

Cell Culture and Viral Strains

The above-mentioned peptides were tested in fetal rhesus kidney (FRhK-4) cell culture described as follows.

Fetal rhesus kidney (FRhK-4) cells were cultured and maintained in MEM medium with 10% fetal bovine serum (10%-MEM, Invitrogen, USA) at 37° C. with 5% $CO_2$. SARS-CoV strain GZ50 was isolated from the nasopharyngeal wash fluid of a patient who suffered from SARS in Guangzhou, China in February 2003, and maintained in the FRhK4 cells (13, 14). Serial passages of the GZ50 strain in FRhK-4 cells consistently yielded cytopathic effects (CPEs) with a titer of $10^7$ $TCID_{50}$/ml. Genomic sequencing (accession number AY304495) and phylogenetic analysis showed that GZ50 lay between the reported Hong Kong strains, and the Canadian and U.S. strains (15).

Peptide Inoculation And Viral Infection

Approximately 5,000 FRhK-4 cells per well were seeded in 96-well plates in 10%-MEM and cultured overnight. After the cells were washed twice with PBS, peptides diluted to different concentrations with MEM (0% FBS), were added to the cultures and incubated at 37° C. for one hour. The cultures were then infected with SARS-CoV GZ50 strain at a multiplicity of infection (MOI) of 0.05. CPE appeared after ~36 hours and peaked ~72 hours post-infection. All experiments were performed in triplicate and were repeated at least three times.

Quantitative RT-PCR

Infectivity of SARS-CoV to the FRhK-4 cells in the presence of the ten 20 mer peptides was assessed by real time PCR. Cells were washed twice with PBS, and total RNA was extracted using RNeasy Mini kit (Qiagen, Hilden, Germany) in accordance with the manufacturer's instructions. Reverse-transcription was performed using random hexamers with the ThermoScript RT system (Invitrogen, CA). Intracellular viral RNA was quantified using quantitative RT-PCR (Q-RT-PCR) (13, 16, 17), using a forward primer 5'-GCTTAGGC-CCTTTGAGAGAGACA-3' (SEQ ID NO.:11) and a reverse primer 5'-GCCAATGCCAGTAGTGGTGTAAA-3' (SEQ ID NO.:12) (final concentration 200 nM), a fluorescent-labeled probe 5'-CCTGATGGCAAACCTTGCAC-3' (SEQ ID NO.: 13) and a phosphate probe 5'-(LC640)CACCTGCTCT- TAATTGTTATTGGCC-3' (SEQ ID NO.:15) (final concentration 800 nM). The real-time quantification was carried out using LC Faststart DNA Master Hyb Probes and LightCycler (Roche Diagnostics, Branchburg, N.J., USA). PCR conditions employed were 95° C. for 10 min. and then 50 cycles at 95° C. for 10 sec., 60° C. for 5 sec., 72° C. for 5 sec., and 40° C. for 30 sec. Ten-fold serial dilutions of plasmid ranging from 1.5 pg/ml to $1.5 \times 10^6$ pg/ml were used as standard and housekeeping gene β-actin was used as an endogenous control to normalize for intersample variation in the amount of total RNA.

Determination of Viral Titres and Identification of Peptides with Antiviral Properties In addition, the infectivity of SARS-CoV to the FRhK-4 cells in the presence of the ten 20mer peptides was assessed by the quantification of viral particles released into the culture medium using a CPE-based $TCID_{50}$ test (17, 18). Culture supernatant collected from SARS-CoV-infected cells 36 hours after viral infection was serially diluted at 10 fold with 1%-MEM and inoculated into FRhK-4 cells in 96-well plates incubated with each peptide at a concentration of 25, 50 and 100 µg/ml for one hour before infection with SARS-CoV at 0.05 MOI. CPE were determined 36 hours post-infection to evaluate peptide-mediated protection from viral infection.

Results were evaluated after 3 days of culture under phase-contrast microscopy, and viral titers were calculated. None of the 10 peptide-treated cells exhibited cytotoxic effects at the concentrations tested, as represented by SEQ ID NO.:8 in FIG. 2A. In untreated cells, the CPEs observed after 36 hours were typified by cell rounding and detachment (FIG. 2B). Significant antiviral effects were observed for peptides SEQ ID NO.:2, SEQ ID NO.:6, SEQ ID NO.:8 and SEQ ID NO.: 10. The most efficacious peptide, SEQ ID NO.:8, effectively protected cells from CPEs at 100 and 50 µg/ml (FIG. 2C), and significantly reduced CPEs at 25 µg/ml (FIG. 2D). Similarly, significant protection was observed for SEQ ID NO.:10 at 100 and 50 µg/ml, and for SEQ ID NO.:2 and SEQ ID NO.:6 at 100 µg/ml, while the other six peptides did not detectably reduce the levels of CPEs, even at a concentration of 100 µg/ml (Table 2).

TABLE 2

Antiviral activities of the peptides determined by CPE

| Peptide | Peptide concentration (µg/ml) | | | | |
|---|---|---|---|---|---|
| | 100 µg | 50 µg | 25 µg | 12.5 µg | 0 µg |
| P1* | + | + | + | + | + |
| P2 | − | ± | + | + | + |
| P3 | + | + | + | + | + |
| P4 | + | + | + | + | + |
| P5 | + | + | + | + | + |
| P6 | − | ± | + | + | + |
| P7 | + | + | + | + | + |
| P8 | − | − | ± | + | + |
| P9 | + | + | + | + | + |
| P10 | − | − | + | + | + |

*P1-P10 are SEQ ID NOs.: 1-10, respectively.

Moreover, the peptide-mediated protection of the FRhK-4 cells from SARS-CoV infection was further indicated by electron microscopy FRhK-4 cells with or without SARS-CoV infections were harvested and fixed in 2.5% glutaraldehyde (Electron Microscopy Sciences, Fort Washington, Pa., USA) for 4 hours and post-fixed in 1% osmium tetroxide for 1 hour. Cells were then transferred to a 1.5 ml tube and centrifuged at 1,000 rpm for 10 min. The supernatant was removed and a liquefied agarose solution (2%, 55-60° C.; Sigma, St. Louis, Mo., USA) was added to the cell pellet. After solidification of the gel, approximately 1 $mm^3$ cubes containing the cell pellet were cut and dehydrated in graded ethanol. The cubes were then embedded in epoxy resin (Polysciences, Warrington, Pa., USA). Ultra-thin sections of 70 nm thickness were prepared and stained with uranyl acetate (Electron Microscopy Sciences, Fort Washington, Pa., USA) and lead citrate (Leica Microsystem 5, Vienna, Austria). Sections were examined under a Philips EM208S electron microscope at 80 kV, and images were marked with a 100 nm scale bar. Results revealed morphology typical of SARS-CoV infections in non-peptide-treated cells (FIG. 2E), whereas no virus was visible in SEQ ID NO.:8-treated cells (FIG. 2F).

Since peptides SEQ ID NO.:3 and SEQ ID NO.:4 that respectively covered variations F360S and N479K (human to animal) located in the identified virus receptor (ACE2) binding region as described (23, 27); and the results showed that peptides SEQ ID NO.:3 and SEQ ID NO.:4 are inactive in this invention, indicating that either these two specific sites are not actively involved in spike-ACE2 binding, or the peptides can not compete with the S protein for binding to ACE2. The active SEQ ID NO.:10 (residues 1161-1180) is derived from the HR2 region (residues 1153-1198) of the S protein. Similar to HIV-1 gp41, the S2 domain of SARS-CoV S protein contains HR1 and HR2 sequence, which are proposed to form a coiled-coil structure (12, 34) that is important for virus-host membrane fusion. The antiviral activity mediated by SEQ ID NO.:10 may be due to peptide blocking the interaction of HR1 and HR2, thereby interrupting membrane fusion. This is consistent with the reports by Liu et al. (12) and Tripet et al. (34). However, SEQ ID NO.:9 (residues 890-909) derived from the HR1 region (residues 892-1013) did not exhibit antiviral activity. The other active peptides SEQ ID NO.:2 (residues 259-278), SEQ ID NO.:6 (residues 598-617) and SEQ ID NO.:8 (residues 737-756) are located neither in the S1-ACE2 binding site (318-510) (24) nor in the HR1 and HR2 regions.

Active Peptides Reduce Viral Titre as Well as Intracellular Viral RNA Level

The antiviral efficacies of the four active peptides were further investigated using $TCID_{50}$ assays with the titration of virus released in the culture media, and by Q-RT-PCR to quantify the levels of cytoplasmic viral RNA in the samples harvested at 36 hours post-infection. As shown in FIG. 3A, the active peptides reduced the number of infectious virions in a dose-dependent manner. The released viral titer was reduced by over 5-fold (to 18% of the untreated control) by treatment with either peptide SEQ ID NO.:2 or SEQ ID NO.:6 at 100 µg/ml, and by about a half at 50 µg/ml, however, no antiviral effects were detected at 25 µg/ml. Peptide SEQ ID:10 reduced the viral titer by over 15-fold (to 6% of the control) at 100 µg/ml, by 10-fold at 50 µg/ml and by a half at 25 µg/ml. Peptide SEQ ID NO.:8 exhibited the strongest antiviral activity, with the viral titer reduced 50-fold (to 2% of the control), 15-fold, and 10-fold at a concentration of 100, 50, and 25 µg/ml, respectively. The 90% inhibition concentration ($IC_{90}$) for these peptides was calculated, and is shown in Table 3. The antiviral efficacy of peptide SEQ ID NO.:8 is the highest, indicated by the lowest $IC_{90}$ value, which is over 4.5-fold lower than that of SEQ ID NO.:2 or SEQ ID NO.:6, and 3-fold lower than that of SEQ ID NO.:10. FIG. 3B shows that the intracellular viral RNA levels were also reduced after treatment with peptides SEQ ID NO.:2, SEQ ID NO.:6, SEQ ID NO.:8 and SEQ ID NO.:10. Consistent with the results from the viral titration assays, SEQ ID NO.:8 exhibited the highest antiviral potency.

TABLE 3

Antiviral effects of the peptides evaluated by $IC_{90}$

| Peptide | $IC_{90}$ (μg/ml ± SD) | Peptide combination | $IC_{90}$ (μg/ml ± SD) |
|---|---|---|---|
| P1* | >500 | P2 + P6 | 59.1 ± 13.5 |
| P2 | 112.5 ± 26.3 | P2 + P8 | 15.7 ± 3.2 |
| P3 | >500 | P2 + P10 | 40.3 ± 12.8 |
| P4 | >500 | P6 + P8 | 9.6 ± 1.9 |
| P5 | >500 | P6 + P10 | 9.9 ± 1.2 |
| P6 | 113.0 ± 27.6 | P8 + P10 | 15.9 ± 4.6 |
| P7 | >500 | P2 + P6 + P8 | 7.5 ± 0.9 |
| P8 | 24.9 ± 6.2 | P2 + P6 + P10 | 8.7 ± 1.1 |
| P9 | >500 | P2 + P8 + P10 | 1.6 ± 0.6 |
| P10 | 73.5 ± 15.7 | P6 + P8 + P10 | 0.9 ± 0.2 |

*P1-P10 are SEQ ID NOs.: 1-10, respectively.

The $IC_{90}$ values were defined as the peptide concentrations that reduced the viral titer by 90%, relative to the untreated control (±standard deviation ("SD")). $IC_{90}$ values were calculated by fitting the logistic equation to data determined for each peptide concentration (performed in triplicate). In a peptide combination, each peptide is in equal amount (weight).

Active Peptides Inhibit The Entry of SARS-CoV Into Cells

To detect whether entry of SARS-CoV into cells is blocked by the peptides, peptide incubation started one hour before viral inoculation. Viral RNA copies in the media and inside the cells were determined by Q-RT-PCR at different time points post-infection. As shown in FIG. 4, compared to peptide-untreated cultures (labeled as the virus control ("VC")), the viral RNA copies were higher in the media of peptide-treated cultures at 1 hour post-infection (1 h-S), but lower in those cells harvested at different time points of post-infection. The virus growth curves in the treated cultures were similar to that in virus control, although they were at lower levels. Furthermore, these active peptides did not show antiviral effects when they were applied to the cultures 1 hour after the virus inoculation and compared viral RNA copies with untreated virus culture control at 6 and 12 post-infection (data not shown). The results indicated that the active peptides could block the entry of the virus to the cells but not inhibit the virus replication.

Synergistic Antiviral Effects Mediated by Peptide Combinations

Combinations of peptides targeting different domains which exhibited synergistic antiviral effects were also investigated. FRhK-4 cells were pre-treated with mixtures of two active peptides one hour before infection, with equal amount of each peptide and total concentrations of 100, 50 and 25 μg/ml, respectively. Samples were collected at 36 hours post-infection for viral titer determination (FIG. 5A) and viral RNA quantification (FIG. 5B). Titration experiments revealed that peptide SEQ ID NO.:2 in combination with SEQ ID NO.:6 reduced the viral titer 1,000-fold (to 0.1% of the control) at 100 μg/ml and 10-fold at 50 μg/ml. Even at a concentration of 25 μg/ml, where no antiviral activities were observed for either peptide individually (FIG. 3A), dual peptide treatment still reduced the viral titer 3-fold (to 32% of the control). The viral titer was reduced 10,000 fold by peptide SEQ ID NO.:6 in combination with SEQ ID:8 at 100 μg/ml. The $IC_{90}$ of SEQ ID NO.:6+SEQ ID:8 is reduced by about 12-fold, as compared with SEQ ID NO.:6 alone ($IC_{90}$ 9.6 μg/ml vs. $IC_{90}$ 113.0 μg/ml), and 2.5-fold as compared to SEQ ID NO.:8 alone ($IC_{90}$ 9.6 μg/ml vs. $IC_{90}$ 24.9 μg/ml) (Table 3). Significant synergistic effects were also observed for other active peptide combinations, but not in active plus inactive peptide combinations (e.g., SEQ ID NO:8+SEQ ID NO:9), as shown in both the calculated $IC_{90}$ values (Table 3) and the relative viral titers (FIG. 5A). These results were further confirmed by Q-RT-PCR assays (FIG. 5B).

The synergistic antiviral effects were investigated by incubating the cells with mixtures containing equal amounts of three peptides applied one hour before viral inoculation. Interestingly, all peptide combinations exhibited greatly improved antiviral potencies (Table 3), reflected in both the levels of released virus (FIG. 6A) and in the quantities of intracellular viral RNA (FIG. 6B). There was essentially complete inhibition of SARS-CoV infection following pre-treatment with the three peptide mixtures at total concentrations of 50 and 25 μg/ml. As SEQ ID NO.:2 and SEQ ID NO.:6 map to the S1 domain, which is involved in binding to the host receptor ACE2 (24, 39), whilst SEQ ID NO.:8 and SEQ ID NO.:10 map to the S2 region that plays a role in virion-membrane fusion (25, 26), these results clearly indicated that combinations of peptides that targeted different domains within the viral S protein significantly enhanced the antiviral effects.

Antiviral Effects of Peptides Derived from Animal Viral Sequences

To determine whether peptides derived from the sequences of animal SARS-CoV-like virus can also inhibit human SARS-CoV infection, peptides derived from the animal virus were synthesized and used to treat FRhK-4 cells before the cells were challenged with human SARS-CoV. Both virus titers in the supernatant (FIG. 7A) and viral RNA in the cells (FIG. 7B) were measured and compared to that of the controls treated with peptides derived from the human virus. Higher viral titers and RNA levels were observed in samples treated with animal peptides than in controls, indicating that the animal peptides were less potent against human SARS-CoV than human peptides. The most significant reduction of the antiviral potency was observed in SEQ ID NO.:6 that the antiviral efficacy of animal SEQ ID NO.:6 is 2 to 4 folds less that that of the human SEQ ID NO.:6 (FIG. 7).

Peplomer Model Construction and Putative 3D Locations of the Active Peptides

To explore how the active peptides mentioned above inhibit viral infections, a molecular modeling of the S glycoprotein in its peplomeric quaternary assembly with the Protein Data Base ("PDB") ID code 1T7G, shown in FIGS. 8A-8F, was used to find a potential mechanism to related to active peptide activity.

The structures of the S1 and S2 domains of the SARS-CoV S protein were retrieved from the PDB (19), with the ID codes 1Q4Z and 1Q4Y, respectively. Docking of the two domains has been manually performed and energetically optimized by using molecular dynamics simulations with Gromacs (20). The reliability of each of the possible peplomer assemblies was assessed using the Prosa II software package (21). Peplomer image construction and exposed surface area ("ESA") calculations were performed using the program MOLMOL (22). The predicted peplomer assembly of the S glycoprotein was deposited in the PDB with the ID code 1T7G (39).

In the model, SEQ ID NO.:2 ("P2") is found to be located on the surface of the S protein adjacent to the ACE2 binding region (FIG. 8A). This suggests that SEQ ID NO:2 does not directly compete for ACE2 binding, but it may hinder the binding site conformation change. The other three active peptides (SEQ ID NO.:6 ("P6"), SEQ ID NO.:8 ("P8") and SEQ ID NO.:10 ("P 10")) are located on the surface of the S1 and S2 domains of the S glycoprotein, and exhibit loop conformations (FIG. 8A). Since these peptides occupy the monomer-monomer interface regions of the S glycoprotein, these peptides may interfere with the peplomer function via competitive binding to the S protein monomer by mimicking regions exposed after ACE2-binding-induced conformation change. These regions may serve as co-receptor binding site, proteinase cleaving site, and/or viron-cell membrane binding site. These peptides may therefore compete with the peplomer for virus-cell membrane interaction (FIGS. 9A-9C).

SEQ ID NO.:8 (residues 737-756), which targets an unknown-function region (residues 673-892) of the S2 domain, exhibited the highest inhibitory activity to the virus infection. Interestingly, it is very close to a putative receptor-binding site (residues 757-761) predicted by Ho et al. (35). By the consideration of the similarity of the infection progression between HIV-1 and SARS-CoV, which involves viral protein-receptor binding, change of viral protein conformation and fusion of virus-cell membrane, residues 737-756 may be an undefined co-receptor (similar to CCR5 and CXCR4 for HIV-1) binding site. SEQ ID NO.:8 may compete with the peplomer for co-receptor interaction (FIG. 9A). This is supported by results showing that SEQ ID NO.:8 also appeared to exert the highest synergistic antiviral effects when used in combination with the other active peptides (Table 3).

Studies with other coronavirus have elucidated that binding of the S1 to soluble viral receptor, or exposure to 37° C. and an elevated pH (pH 8.0), can induce a conformational change accompanied by the cleavage of S1 and S2, which might be involved in triggering virus-cell membrane fusion (36-38). The active peptide SEQ ID NO.:6 (residues 598-617) is located on the surface of S1 domain where it is close to the S1-S2 connection site (FIGS. 8A and 8F). Its antiviral activity may be attributed to the binding of SEQ ID NO.:6 to the S protein monomer interfering with the cleavage of S1 and S2, resulting in the failure of subsequent fusion between viral envelope and host cell membrane (FIG. 9B).

The synergistic effect of two and three peptide combinations suggests that increased disruption of peplomer function can be achieved by simultaneously blocking multiple protein-protein or protein-membrane interaction sites. These peptides may distort the peplomer assembly or conformation by competitive binding to the S protein monomer (FIG. 9C).

Two common features were found to be associated with the active peptides (SEQ ID NOs.:6, 8 and 10). First, they are located on the surface of the S1 and S2 domains where the monomers contact each other. Second, these active peptides exhibit loop conformations. On the contrary, the inactive peptides are located at exposed peplomer surfaces (SEQ ID NO.:1, SEQ ID NO.:3 and SEQ ID NO.:4; not shown) and exhibit helical structures (SEQ ID NO.:1, SEQ ID NO.:3, SEQ ID NO.:4, SEQ ID NO.:5, SEQ ID NO.:7 and SEQ ID NO.:9). Active peptides are the only ones which exhibit a loop conformation, suggesting a loop conformation is necessary for ease of access of the peptide to the S protein monomer or a co-receptor. Consistent with this model, the inactive peptides either belong to exposed surface regions of the peplomer (SEQ ID NO.:1, SEQ ID NO.:3 and SEQ ID NO.:4) and/or exhibit helical conformation (SEQ ID NO.:1, SEQ ID NO.:3, SEQ ID NO.:4, SEQ ID NO.:5, SEQ ID NO.:7 and SEQ ID NO.:9).

SEQ ID NOs: 6, 8 and 10, the only peptides which reproduce loop conformations of the peplomer, are the ones which can more easily interfere with the peplomer assembly by competitive binding to the S protein monomer. More ordered secondary structure elements, such as the proposed helices formed by SEQ ID NOs:1, 3, 4, 5, 7 and 9 have no antiviral activities. Peptides reproducing exposed surface regions of the peplomer (SEQ ID NOs.1, 3 and 4) are total inactive since no interference of the peplomer quanternary structure stability can be induced by their presence. Thus, active peptides bind to the peplomer in critical regions for the conformational changes that are necessary for the membrane fusion process.

REFERENCES

1. Peiris, J. S., et al., *Lancet* 361, 1319-1325 (2003).
2. Rota, P. A., et al., *Science* 300, 1394-1399 (2003).
3. Marra, M. A., et al., *Science* 300, 1399-1404 (2003).
4. Fouchier, R. A., et al., *Nature* 423, 240 (2003).
5. Guan, Y., et al., *Science* 302, 276-278 (2003).
6. Holland, J. J., et al., *J. Viol.* 65, 2960-2967 (1991).
7. "The Chinese SARS Molecular Epidemiology Consortium," *Science* 303, 1666-1669 (2004).
8. Derdeyn, C. A., et al., *J. Virol.* 75, 8605-8614 (2001).
9. Sia, S. K., et al., *Proc. Natl. Acad. Sci. USA.* 99, 14664-14669 (2002).
10. Medinas, R. J., et al., *J Virol* 76, 9079-9086 (2002).
11. Pinon, J. D., et al., *J. Virol.* 77, 3281-3290 (2003).
12. Liu, S., et al., *Lancet.* 363, 938-947 (2004).
13. He, M. L., et al., *JAMA* 290, 2665-2666 (2003).
14. Zhong, N. S., et al., *Lancet* 362, 1353-1358 (2003).
15. Guan, Y., et al., *Lancet.* 363, 99-104 (2004).
16. He, M. L., et al., *Biochem. Biophys. Res. Commun.* 297, 185-192 (2002).
17. He, M. L., et al., *Biochem. Biophys. Res. Commun.* 295, 1102-1107 (2002).
18. Zheng, B., et al., *Emerg. Infect. Dis.* 10, 176-178 (2004).
19. Berman, H. M., et al., *Nucleic Acids Research* 28, 235-242 (2000).
20. Berendsen, H. J. C., et al., *Comp. Phys. Comm.* 91, 43-56 (1995).
21. Sippl, M. J. 17, 355-362 (1993).
22. Koradi, R., et al., *J. Mol. Graph.* 14, 51-55 (1996).
23. Li, W., et al., *Nature* 426, 450-454 (2003).
24. Wong, S. K., et al., *J. Biol. Chem.* 279, 3197-3201 (2004).
25. Matsuyama, S. and Taguchi, F., *Virology* 295,160-171 (2002).
26. Taguchi, F. and Shimazaki, Y. K., *J. Gel. Virol.* 81, 2867-2871 (2000).
27. Sui, J., et al., *Proc. Natl. Acad. Sci. USA* 101, 2536-2541 (2004).
28. Spiga, O., et al., *Biochem. Biophys. Res. Commun.* 310, 78-83 (2003).
29. Delmas, B. and Laude, H., *J. Virol.* 64, 5367-5375 (1990).
30. Lewicki, D. N. and Gallagher, T. M., *J. Biol. Chem.* 277, 19727-19734 (2002).
31. Sauter, N. K., et al., *Biochemistry* 31, 9609-9621 (1992).
32. Lin, Y., et al., *Antiviral Therapy* 9, 287-289 (2004).
33. Babcock, G. J., et al., *J. Virol.* 78, 4552-4560 (2004).
34. Tripet, B., et al., *J. Biol. Chem.* 279, 20836-20849 (2004).
35. Ho, T. Y., et al., *Biochem. Biophys. Res. Commun.* 313, 938-947 (2004).
36. Gallagher, T. M., *J. Virol.* 71, 3129-3137 (1997).
37. Holmes, K. V., et al., *Adv. Exp. Med. Biol.* 494, 193-198 (2001).
38. Sturman, L. S., et al., *J. Virol.* 64, 3042-3050 (1990).
39. Bernini, A, et al., *Biochem. Biophys. Res. Communi.* 325, 1210-1214 (2004).
40. World Health Organization ("WHO"), *Communicable Disease Surveillance & Response (CSR): Severe Acute Respiratory Syndrome.* www.who.int/csr/sars/en.

What is claimed is:

1. A method for locating one or more site(s) of a severe acute respiratory syndrome-associated coronavirus (SARS-CoV) S protein responsible for facilitating viral infection in a cell, wherein said method comprises contacting the cell, prior to viral infection, with a peptide consisting of SEQ ID NO:6 and SEQ ID NO:8, wherein said method further comprises contacting the cells with a SARS-CoV virus, ascertaining whether viral infection of the cell is reduced compared to infection of the cell in the absences of the peptide, and, when infection is reduced, identifying the site(s) of the SARS-CoV virus blocked by the peptide.

2. The method of claim 1, wherein the cell is from a primate or a human.

* * * * *

UNITED STATES PATENT AND TRADEMARK OFFICE
CERTIFICATE OF CORRECTION

PATENT NO.       : 7,491,489 B2                                    Page 1 of 1
APPLICATION NO.  : 11/262044
DATED            : February 17, 2009
INVENTOR(S)      : Zheng et al.

It is certified that error appears in the above-identified patent and that said Letters Patent is hereby corrected as shown below:

Title Page,
Assignee (73), "Hong Knog" should read --Hong Kong--.

Signed and Sealed this

Fifth Day of May, 2009

JOHN DOLL
*Acting Director of the United States Patent and Trademark Office*